US012806139B2

(12) United States Patent
Lizonova et al.

(10) Patent No.: US 12,806,139 B2
(45) Date of Patent: Nov. 24, 2026

(54) METHOD FOR PREPARING AN AQUEOUS NANOCRYSTALLINE SUSPENSION CONTAINING NANOCRYSTALS OF PHARMACEUTICALLY ACTIVE INGREDIENT AND A COMBINATION OF STABILIZERS, AQUEOUS NANOCRYSTALLINE SUSPENSION AND METHODS OF USE THEREOF

(71) Applicant: Vysoka skola chemicko-technologicka v Praze, Prague (CZ)

(72) Inventors: Denisa Lizonova, Prague (CZ); Frantisek Stepanek, Lhotka (CZ); Martin Balouch, Banov (CZ); Filip Hladek, Prague (CZ); Stanislav Chvila, Veletiny (CZ); Ondrej Navratil, Prague (CZ); Adela Brejchova, Strakonice (CZ); Eva Králová, Litvinov (CZ)

(73) Assignee: Vysoka skola chemicko-technologicka v Praze, Prague (CZ)

( * ) Notice: Subject to any disclaimer, the term of this patent is extended or adjusted under 35 U.S.C. 154(b) by 411 days.

(21) Appl. No.: 18/214,068

(22) Filed: Jun. 26, 2023

(65) Prior Publication Data

US 2023/0414502 A1 Dec. 28, 2023

(30) Foreign Application Priority Data

Jun. 28, 2022 (EP) .................................... 22181609

(51) Int. Cl.
*A61K 9/08* (2006.01)
*A61K 45/06* (2006.01)
*B82Y 5/00* (2011.01)

(52) U.S. Cl.
CPC ................ *A61K 9/08* (2013.01); *A61K 45/06* (2013.01); *B82Y 5/00* (2013.01)

(58) Field of Classification Search
CPC ............. A61K 9/08; A61K 45/06; B82Y 5/00
See application file for complete search history.

(56) References Cited

FOREIGN PATENT DOCUMENTS

| | | | | |
|---|---|---|---|---|
| CN | 102579337 A * | 7/2012 | | |
| WO | WO-2004043363 A2 * | 5/2004 | ................ | A61P 9/00 |

OTHER PUBLICATIONS

Machine translation for CN-102579337-A (Year: 2012).*
Composition of Soybean Lecithin—Soy Lecithin Manufacturer & Supplier (site accessed Aug. 2025) (Year: 2025).*
Hong et al.; High drug payload curcumin nanosuspensions stabilized by mPEG-DSPE and SPC: in vitro and in vivo evaluation; Taylor & Francis; Drug Deliv, 2017; 24(1): 109-120 (Year: 2017).*
Imran et al.; Docetaxel: An update on its molecular mechanisms, therapeutic trajectory and nanotechnology in the treatment of breast, lung and prostate cancer; Elsevier; Journal of Drug Delivery Science and Technology 60 (2020) 101959 (Year: 2020).*
Liu et al.; Nanosuspensions of poorly soluble drugs: Preparation and development by wet milling; Elsevier; International Journal of Pharmaceutics 411 (2011) 215-222 (Year: 2011).*
Malamatari et al.; Pharmaceutical nanocrystals: production by wet milling and applications; Elsevier; Drug Discovery Today, vol. 23, No. 3, Mar. 2018, 534-547 (Year: 2018).*

* cited by examiner

*Primary Examiner* — Robert A Wax
*Assistant Examiner* — John W Lippert, III
(74) *Attorney, Agent, or Firm* — Notaro, Michalos & Zaccaria P.C.

(57) ABSTRACT

A method for preparing an aqueous nanosuspension of API, containing the steps of preparing an aqueous suspension and a crystalline API selected from the group containing API having intrinsic solubility in water of at most 50 mg/L, and having log P of at least 4, and a combination of at least two phospholipidic stabilizing agents containing lipophilic carbohydrate chains having from 6 to 20 carbon atoms; where at least one of the stabilizing agents is PEG-coupled phospholipid of general formula (I), (I)

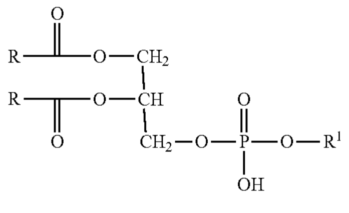

16 Claims, 18 Drawing Sheets

METHOD FOR PREPARING AN AQUEOUS NANOCRYSTALLINE SUSPENSION CONTAINING NANOCRYSTALS OF PHARMACEUTICALLY ACTIVE INGREDIENT AND A COMBINATION OF STABILIZERS, AQUEOUS NANOCRYSTALLINE SUSPENSION AND METHODS OF USE THEREOF

STATE OF ART

The present invention relates to a method for formation of a colloidally stable aqueous nanocrystal suspension, which may be used for development, screening and testing of natural or synthetic bioactive compounds with low solubility in water.

BACKGROUND ART

The majority of newly developed drug candidates are poorly soluble in water. When bioactivity is tested for such compounds, it is necessary to dissolve them in a solvent such as DMSO, followed by adding such solution to aqueous cell culture medium (typically up to 1% v/v DMSO in tested sample). Addition of DMSO solution to water solution often causes supersaturation and subsequent precipitation/crystallization of the solute. The consequence of precipitation is a reduction of the actual concentration of molecularly dissolved drug in the aqueous phase. The solid precipitate present in the tested sample unpredictably influences the bioactivity results (e.g. caused by adsorption of proteins to the surface of precipitated particles or by physical contact of sedimented precipitate with the cells). Moreover, the presence of DMSO in solution may influence the fluidity of cell membranes, which leads to greater uptake of the tested compound into the cells. The above described processes therefore have both synergistic and antagonistic effects, neither of which is desired and the results thus obtained are very difficult to correlate with the behavior of the tested compound in a living organism when tested in vivo in preclinical studies. Consequently, a large number of false positives or false negatives are obtained, with costly consequences for drug candidate screening.

Nanocrystals represent a novel pharmaceutical dosage form that finds use in both oral and parenteral drug formulations. While the oral nanocrystal-based drug formulations strongly profit from the increased dissolution rate and improved bioavailability, intravenously administered nanocrystals can be used for targeted drug delivery. Nanocrystals for pharmaceutical application are usually prepared by precipitation or wet-milling techniques. In order to preserve the nano-scaled size of the final product and prevent undesired recrystallization or Ostwald ripening, the addition of stabilizing agents is vital. The application of stabilizers in the form of surfactants/amphiphiles or polymeric coatings is necessary also to withstand the challenging environment of the human body. The nanocrystals stabilization is usually based on electrostatic repulsion or steric hindrance. The eligible stabilizer should not only provide colloidal stability of nanocrystals but may further affect the dissolution rate of the condensed drug core.

Phospholipids are a class of lipids whose molecule has a hydrophilic "head" containing a phosphate group and two hydrophobic "tails" derived from fatty acids, joined by an alcohol residue (usually a glycerol molecule). The phosphate group can be modified with simple organic molecules such as choline, ethanolamine or serine. In the case of synthetic phospholipids, the phosphate group can be further modified with poly(ethylene glycols) (PEG) of a wide range of molecular weights with the possibility of adding reactive groups to the distal end of the PEG, which allows for covalent coupling of various ligands.

Phospholipids are a key component of all cell membranes. They can form lipid bilayers because of their amphiphilic characteristic. In eukaryotes, cell membranes also contain another class of lipid, sterol, interspersed among the phospholipids. The combination provides fluidity in two dimensions combined with mechanical strength against rupture. Phospholipids are known to have great biocompatibility, and have found applications in nanotechnology, medicinal applications, and materials science. The most common medicinal application of phospholipids is the preparation of liposomes—spherical vesicles consisting of a phospholipidic bilayer enclosing a hydrophilic lumen (therefore allowing for encapsulation of both hydrophilic substances—in the lumen, and lipophilic substances—in the lipidic bilayer). Liposomes are used in cancer treatment, where they provide advantages of improved drug pharmacokinetics and specific accumulation in tumors and thus improve treatment efficacy.

Approaches to dissolution rate enhancement of poorly water-soluble active pharmaceutical ingredients (APIs) belong into two main categories:

Those based on solid-state chemistry (e.g., metastable polymorphs, salts, co-crystals or amorphous solid dispersions), and those utilizing nanoformulations. In the latter category, one possibility is to incorporate the API into nano-sized carrier particles such as solid lipid nanoparticles, polymeric nanoparticles, or above-mentioned liposomes. However, this approach is limited by the affinity of the API to the matrix material of the nanocarrier, and in practice, only a relatively small number of substances are suitable for such formulations. Moreover, the final drug loading in the carrier is rather low (reaching units or low tens of percent). Another possibility is to retain the bulk crystalline API and reduce its particle size to sub-micron dimensions, forming API nanocrystals. Pharmaceutical nanosuspensions can be produced e.g. by wet stirred media milling. The high surface-to-volume ratio of nanocrystals improves their dissolution characteristics since the rate of dissolution is directly proportional to the specific surface area of the API. The drug loading of the nanocrystals can reach >90% since the nearly whole particle is created by the pure crystalline API. Moreover, the surface modification of nanocrystals can provide additional functionality such as active targeting.

A common practice in bioactivity and cytotoxicity studies of poorly water-soluble substances is their dissolution in DMSO and subsequent addition to the aqueous cell culture media in a specified concentration series. However, such approach often leads to uncontrolled precipitation, the formation of solid particles with undefined size distribution (often comparable to the cell size), unknown surface properties, and unpredictable colloidal stability, dissolution profile and cell uptake rate. This makes the subsequent interpretation and comparison of such studies questionable.

When considering the nanocrystals of poorly soluble drugs as solid nanoparticles, their biocompatibility and interaction with the immune system must not be overlooked. Therefore, apart from cytotoxicity and bioactivity tests on target cells, which are conventionally done with true drug solutions, investigation of the non-specific macrophage uptake is common when investigating the biocompatibility of nanoparticulate drug delivery system.

Therefore, there exists a constant need for a controlled formation of API nanocrystals and their stabilization in a form of nanosuspension, which would behave as a "pseudo-solution" and could be used in drug screening experiments and bioactivity tests in a wide concentration range regardless of the thermodynamic solubility of the investigated compound. If proven sufficiently efficient for tested bioactivity, the formulated nanocrystals can be directly moved to following in vivo testing without the need to reformulate the API (reformulation would lead to change in the dissolution behavior and is costly). Such an approach should also increase the agreement of the results from in vitro and in vivo, since both of these tests would be carried out with the same formulation.

DISCLOSURE OF INVENTION

The present invention overcomes the drawbacks of the background art, and presents a method for the formation of a colloidally stable nanocrystal suspension of API, which effectively behaves as a "pseudo-solution" in that it enables to test bioactivity in a wide concentration range regardless of the thermodynamic solubility of the investigated API compound. The nanocrystal suspension of API enables to relate the process of bioactivity testing of API in vitro, and testing of a final pharmaceutical formulation of API in a follow-up preclinical testing in vivo. It was found by the inventors that by suitable surface stabilization it is possible to create a colloidally stable API nanocrystals suspension that enhances the bioactivity of a naturally occurring compound to levels comparable with clinically approved cytostatics. The stabilization of nanocrystals occurs with phospholipids, which are known to have great biocompatibility and can be easily used for direct covalent coupling. Pharmaceutical nanocrystals represent a promising new formulation that combines the benefits of bulk crystalline materials and colloidal nanoparticles. To be applied in vivo, nanocrystals must meet several criteria, namely colloidal stability in physiological media, non-toxicity to healthy cells, avoidance of macrophage clearance, and bioactivity in the target tissue.

The API nanosuspension is prepared by wet milling using specific combination of steric and ionic stabilizers from the group of phospholipids in combination with a further stabilizer on the basis of polyethylene glycol. Resulting API nanocrystal suspensions were proved to be successful in all evaluated criteria: they were colloidally stable in all tested media, and exhibited low macrophage clearance. Preparation of phospholipid-stabilized nanocrystal suspensions allows for the conversion of poorly soluble compounds into highly effective "solution-like" drug delivery systems at pharmaceutically relevant drug concentrations.

The nanocrystalline suspensions according to the present invention can be prepared on a very small scale (below 100 mg/batch), which is a great advantage for newly developed API molecules (in vitro testing can take place before or during the upscale synthesis of the substance).

The prepared nanocrystals are stable in buffers and cell media in a wide range of concentrations and allow to test APIs up to about 60 mg/mL without the need for DMSO or other non-aqueous solvents. It was also observed by the inventors that the effective $IC_{50}$ inhibitory concentrations of API are orders of magnitude lower, because nanocrystals significantly improve the solubility of the API due to the large surface area. In practice, this means that even if some molecules have determined $IC_{50}$ values outside a certain concentration range, it is only that the substance has been tested inappropriately, precipitated and dissolved poorly. For many substances, $IC_{50}$ values reported in the literature vary greatly as a consequence of uncontrolled precipitation from DMSO. In contrast, colloidally stable nanocrystal suspension makes it possible to obtain reproducible results with low variance. Moreover, using nanosuspensions of API instead of their DMSO solutions in cell line testing may lead to determining API efficiency even where no efficiency has been observed before and the relevant APIs have been taken out from the screening. It was observed by the inventors, that in some cases (when e.g. abiraterone acetate or telmisartan were used as API), it was not possible to reach 500 μg/mL API concentration together with total DMSO content of maximum 1% (1% DMSO is top limit standard in biochemical testing considering the DMSO toxicity and effect on the cell viability and performance) and therefore these substances could only be tested at lower concentration (100 μg/mL). The ability to achieve effective API concentrations above thermodynamic solubility in a reproducible way without the risk of uncontrolled precipitation presents the most important advantage of nanocrystals over DMSO solution, since the nanocrystal samples can be prepared and tested at significantly higher concentrations (e.g. 500 μg/mL) even in cases where the DMSO solvents would not be accepted for in vitro testing.

Abbreviations and Definitions

Abirat—abiraterone acetate
Telmi—telmisartane
Ivacaf—ivacaftor
Cande—candesartan cilexetil
Atory—atorvastatin
CC—curcumin
NC—nanocrystals
DPPG—dipalmitoylphosphatidylglycerol
HPMC—hydroxypropyl methylcellulose
SDS—sodium dodecyl sulfate
API—active pharmaceutical ingredient=a compound having a biological activity
DPPC—dipalmitoylphosphatidylcholine
PEG—polyethylene glycol
Poloxamer P188—poly(ethylene glycol)-block-poly(propylene glycol)-block-poly(ethylene glycol)
DMSO—dimethyl sulfoxide
$IC_{50}$—half maximal inhibitory concentration
log P—partition coefficient of lipophilicity
PE—phosphatidylethanolamine
LPE—lysophosphatidylethanolamine
PC—phosphatidylcholine
LPC—lysophosphatidylcholine
PA—phosphatidic acid
LPA—lysophosphatidic acid
PG—phosphatidylglycerol
LPG—lysophosphatidylglycerol
PI—phosphoinositide
LPI—lysophosphoinositide
PS—phosphatidylserine
LPS—lysophosphatidylserine
DMPE—1,2-dimyristoyl-sn-glycero-3-phosphoethanolamine
MPEG2000-DMPE—1,2-dimyristoyl-sn-glycero-3-phosphoethanolamine-n-PEG-2000
MPEG-DMPE=1,2-dimyristoyl-sn-glycero-3-phosphoethanolamine-n-PEG
Tween 80—polysorbate 80, a nonionic surfactant and emulsifier MEM—minimal essential medium=a synthetic cell culture medium used to maintain cells in tissue culture, based on $CaCl_2$, KCl, $MgSO_4$, NaCl, $Na_3PO_4$, $NaHCO_3$ and glucose.

Alkyl shall be understood as a hydrocarbon chain derived from an alkane by removing one hydrogen. It may be linear or branched.

Alkenyl shall be understood as a hydrocarbon chain comprising at least one carbon-carbon double bond, derived from an alkene by removing one hydrogen. It may be linear or branched. PEG-coupled phospholipid is a phospholipid attached to one end of a polyethylene glycol, wherein the polyethylene glycol chain has molar mass in the range of from 350 to 5000 (corresponding to from 8 to 125 monomeric ethylene oxide units).

Non-PEG-coupled phospholipid is a phospholipid not attached to polyethylene glycol chain. Intrinsic solubility shall be understood as a solubility of the compound in its free acid or free base form, measured at a pH where the substance is uncharged.

Aqueous suspension shall be understood as a heterogenous mixture of solid particles and water or water-based buffers, such as phosphate buffer (PBS).

An object of the present invention is a method for preparing an aqueous nanosuspension of API (meaning an aqueous nanocrystalline suspension of API), comprising the following steps: (a) preparing an aqueous suspension comprising a crystalline API selected from the group comprising API having intrinsic solubility in water of at most 50 mg/L (calculated according to Hou, T. J., Xia, K., Zhang, W., & Xu, X. J. (2004). ADME evaluation in drug discovery. 4. Prediction of aqueous solubility based on atom contribution approach. *Journal of chemical information and computer sciences,* 44(1), 266-275; implemented to ChemAxon solubility calculation plugin), and having log P of at least 4 (calculated according to Viswanadhan, V. N., Ghose, A. K., Revankar, G. R., & Robins, R. K. (1989). Atomic physicochemical parameters for three dimensional structure directed quantitative structure-activity relationships, 4. Additional parameters for hydrophobic and dispersive interactions and their application for an automated superposition of certain naturally occurring nucleoside antibiotics. *Journal of chemical information and computer sciences,* 29(3), 163-172; implemented in ChemAxon logP calculation plugin), and a combination of at least two stabilizing agents, selected from the group of phospholipids containing lipophilic carbohydrate chains comprising from 6 to 20 carbon atoms;

wherein at least one of the stabilizing agents is selected from the group of PEG-coupled phospholipids of general formula (I), (I)

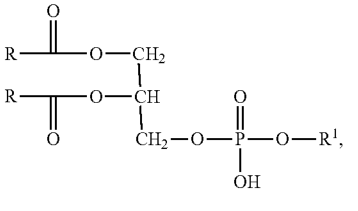

wherein R is independently selected from (C6 to C20)alkyl and (C6 to C20)alkenyl;

$R^1$ is

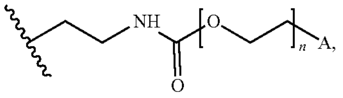

wherein n is an integer in the range of from 8 to 125 (corresponding to PEG molecular mass in the range of from 350 to 5000 g/mol); and wherein A is selected from the group comprising —OH, —$OCH_3$, —$NH_2$, —NH—(C═O)—$CH_2$—$CH_2$—COOH, —NH—(C═O)—$CH_2$—$CH_2$—SH; —$CH_2$COOH, —$N_3$, —O—$CH_2$COOH, —$CH_2$CH(═O);

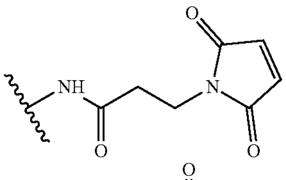

,

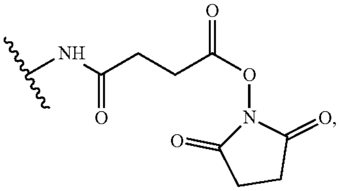

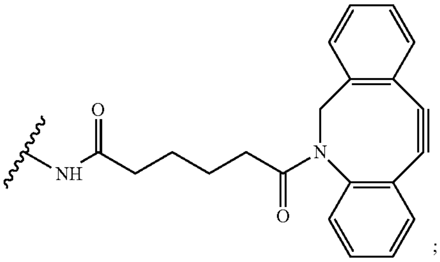

;

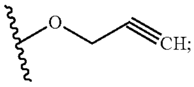

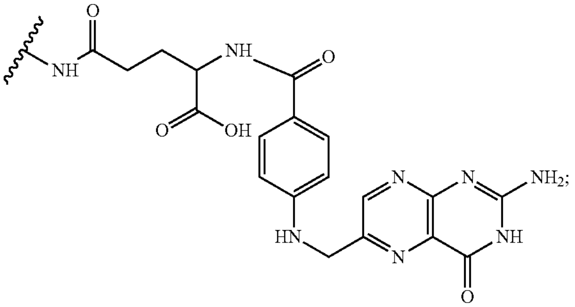

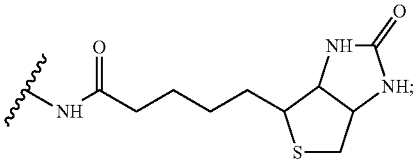

wherein the weight ratio of API to the stabilizing agent combination in step (a) is from 20:1 to 1:1, preferably the weight ratio of API to the stabilizing agent combination in step (a) is in the range of from 10:1 to 1:1, more preferably from 2:1 to 1:1, even more preferably from 3:2 to 1:1;

(b) placing milling balls, preferably $ZrO_2$ milling balls, even more preferably $ZrO_2$ milling balls with diameter in the range of from 0.2 to 0.7 mm, into the aqueous suspension from step (a); and (c) milling the aqueous suspension of step (b) to obtain nanocrystalline API suspension, wherein the size of the resulting API nanocrystals is at most 300 nm, determined using Dynamic Light Scattering (Microtrac NANO-flex, demineralized water, 20° C.).

The parameters of water solubility were determined using Hou, T. J., Xia, K., Zhang, W., & Xu, X. J. (2004). ADME evaluation in drug discovery. 4. Prediction of aqueous solubility based on atom contribution approach. *Journal of chemical information and computer sciences,* 44(1), 266-275; implemented to ChemAxon solubility calculation plugin. Viswanadhan, V. N., Ghose, A. K., Revankar, G. R., & Robins, R. K. (1989). Atomic physicochemical parameters for three dimensional structure directed quantitative structure-activity relationships. 4. Additional parameters for hydrophobic and dispersive interactions and their application for an automated superposition of certain naturally occurring nucleoside antibiotics. *Journal of chemical information and computer sciences,* 29(3), 163-172; implemented in ChemAxon logP calculation plugin.

The parameters of the partition coefficient of lipophilicity log P were determined using Viswanadhan, V. N., Ghose, A. K., Revankar, G. R., & Robins, R. K. (1989). Atomic physicochemical parameters for three dimensional structure directed quantitative structure-activity relationships. 4. Additional parameters for hydrophobic and dispersive interactions and their application for an automated superposition of certain naturally occurring nucleoside antibiotics. *Journal of chemical information and computer sciences,* 29(3), 163-172; implemented in ChemAxon logP calculation plugin. Hou, T. J., Xia, K., Zhang, W., & Xu, X. J. (2004). ADME evaluation in drug discovery. 4. Prediction of aqueous solubility based on atom contribution approach. *Journal of chemical information and computer sciences,* 44(1), 266-275; implemented to ChemAxon solubility calculation plugin.

If higher amounts of phospholipid stabilizing agents are used (where the weight ratio of API to the stabilizing agent combination in step (a) is lower than 1:1), API is dissolved in phospholipids, thus forming a nanoemulsion rather than nanocrystalline suspension. Such emulsions are not suitable as "pseudo-solutions" for testing on living cells without the need of use of DMSO or any other organic solvent.

In a preferred embodiment, step (c) is followed by a step (d), wherein the resulting suspension from step (c) is sterile-filtered with a filter of the average pore size of 200 nm (preferably the input API suspension concentration is in the range of from 1 to 10 mg/mL). The sterile filtration ensures that the resulting nanosuspension does not contain any bacteria or other non-sterile impurities, and, moreover, ensures that no nanocrystals larger than 200 nm are present in the resulting nanosuspension. The nanocrystal size below or equal to 200 nm has the advantage that no sedimentation occurs in the resulting nanosuspension.

Preferably, the nanocrystal size in the nanosuspension is in the range of from 1 to 200 nm.

The colloidal stability of the nanosuspension was confirmed by measuring particle size in a solution of a need (buffer, cell culture medium or other) using DLS (Microtrack NANO-flex, 10 mM phosphate buffered saline pH 7.4, 20° C.), wherein the obtained particle size did not exceed 1000 nm.

In one embodiment, the aqueous nanosuspension from step (c) or (d) may be dried. Drying may be performed by any conventional drying methods, suitable for the API contained in the nanosuspension (e.g. freeze-drying, spray drying, fluid-bed drying, vacuum contact drying).

In another embodiment, the aqueous nanosuspension from step (c) or (d) may be coated onto a carrier to form composite particles, or can be used for fluidized bed granulation. The resulting powder may be further used in preparation of oral dosage forms of a pharmaceutical composition. Suitable carriers may be selected from the group comprising microcrystalline cellulose, sugar pellets, tartaric acid pellets and other materials and excipients commonly used for fluid bed coating, drum coating or spray coating.

Preferably the crystalline API in step (a) has intrinsic solubility (calculated by ChemAxon solubility plugin) lower than 50 mg/L, more preferably lower than 40 mg/L, even more preferably lower than 30 mg/L, even more preferably lower than 25 mg/L, for example from 0.001 to 24 mg/L. The lower the intrinsic solubility of API is, the more favorable milling properties the particular API has (providing smaller particles after standard milling time).

Preferably, log P of the crystalline API in step (a) is in the range of from 4 to 10, more preferably from 4.2 to 10, most preferably from 4.4 to 10.

Preferably, the PEG-coupled phospholipid has general formula (I), wherein R is independently selected from linear (C6 to C20)alkyl and linear (C6 to C20)alkenyl; more preferably R is independently selected from the group comprising $—(CH_2)_z—CH_3$, wherein z is an integer in the range of from 10 to 17; $—(CH_2)_p—(CH{=}CH—CH_2)_q—(CH_2)_r—CH_3$, wherein p, r are independently an integer from 1 to 8; q is an integer from 1 to 5; even more preferably R is selected from $—(CH_2)_{14}—CH_3$; $—(CH_2)_{16}—CH_3$; $—(CH_2)_3—(CH{=}CH—CH_2)_4—(CH_2)_3—CH_3$; and $—(CH_2)_7—CH{=}CH—(CH_2)_7—CH_3$.

More preferably, both substituents R are the same. Most preferably, both substituents R are the same, and selected from $—(CH_2)_{14}—CH_3$; $—(CH_2)_{16}—CH_3$; $—(CH_2)_3—(CH{=}CH—CH_2)_4—(CH_2)_3—CH_3$; and $—(CH_2)_7—CH{=}CH—(CH_2)_7—CH_3$.

Preferably, the PEG-coupled phospholipid has general formula (I), wherein $R^1$ is

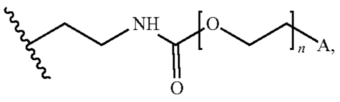

wherein A is as defined above and n is an integer in the range of from 25 to 115, more preferably n is in the range of from 30 to 100, even more preferably n is in the range of from 40 to 80, most preferably n is 50 (corresponding to PEG molecular mass of 2000 g/mol). Most preferably, $R^1$ is

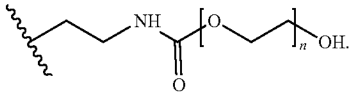

Preferably, the molar ratio of the PEG-coupled phospholipids of general formula (I) to the other phospholipids (non-PEG-coupled) is in the range of from 1:49 to 1:4, more preferably from 1:24 to 1:9, the most preferably from 1:19 to 2:23. This corresponds to the content of the PEG-coupled phospholipids of general formula (I) in the range of from 2 to 20 mol. %, more preferably from 4 to 10 mol. %, most preferably from 5 to 8 mol. %, related to the overall content of phospholipidic stabilizing agents.

A surprising effect of the present invention is that nanosuspensions prepared using the above described method, therefore stabilized by the combination of non-PEG-coupled phospholipids and PEG-coupled phospholipids, are extremely colloidally stable in a wide range of API concentrations (up to about 100 mg/mL) and conditions (presence of salts and proteins, cell culture media).

In one embodiment of the method, the concentration of crystalline API in the aqueous suspension in step (a) is in the range of from 10 mg/mL to 100 mg/mL, preferably from 15 mg/mL to 80 mg/mL, more preferably from 20 mg/mL to 70 mg/mL, more preferably from 30 mg/mL to 65 mg/mL, most preferably from 40 mg/mL to 60 mg/mL.

In one embodiment of the method, in step (b) there is at least 2 g of the $ZrO_2$ milling balls used per 1 ml of the aqueous suspension from step (a), preferably from 3 to 10 g of the $ZrO_2$ milling balls, more preferably from 4 to 8 g of the $ZrO_2$ milling balls, most preferably from 5 to 6 g of the $ZrO_2$ milling balls per 1 ml of the aqueous suspension from step (a). Preferably, the $ZrO_2$ milling balls have diameter in the range of from 0.2 to 0.7 mm, more preferably from 0.4 to 0.5 mm Preferably, the milling in step (c) is carried out for at least 12 hours by means of stirring at 400 to 1000 rpm, preferably at 600 rpm. Under these conditions, the size of the resulting nanocrystals of API is below 300 nm.

In one embodiment of the method, API is selected from the group comprising curcumin, abiraterone acetate, ivacaftor, atorvastatin, candesartan cilexetil, and telmisartan.

In one embodiment, the non-PEG-coupled phospholipidic stabilizing agent has the general formula (II)

(II)

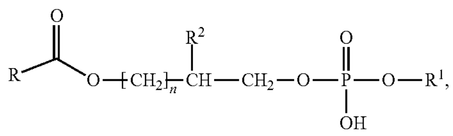

wherein n is an integer from 1 to 3;

$R^1$ is selected from the group comprising H; $—(CH_2)_m—NH_2$; $—(CH_2)_m—CH(OH)—CH_2(OH)$; $—(CH_2)—CH(COOH)—NH_2$;

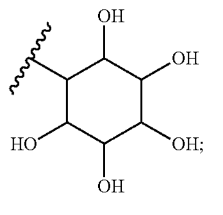

wherein m is an integer from 1 to 3;

$R^2$ is selected from —OH; —O—C(═O)—R;

R is independently selected from (C6 to C20)alkyl and (C6 to C20)alkenyl; preferably R is independently selected from linear (C6 to C20)alkyl and linear (C6 to C20)alkenyl; more preferably R is independently selected from the group comprising $—(CH_2)_z—CH_3$, wherein z is an integer in the range of from 10 to 17; $—(CH_2)_p—(CH═CH—CH_2)_q—(CH_2)_r—CH_3$, wherein p, r are independently an integer from 1 to 8; q is an integer from 1 to 5; even more preferably R is selected from $—(CH_2)_{14}—CH_3$; $—(CH_2)_{16}—CH_3$; $—(CH_2)_3—(CH═CH—CH_2)_4—(CH_2)_3—CH_3$; and $—(CH_2)_7—CH═CH—(CH_2)_7—CH_3$.

R may be the same or different. Preferably R is the same. Preferably, $R^2$ is —O—C(═O)—R.

In one preferred embodiment, the non-PEG-coupled phospholipidic stabilizing agent in the combination of stabilizers in step (a) has the general formula (II), wherein n is 1; $R^1$ is selected from the group comprising H; $—(CH_2)_2—NH_2$; $—CH_2—CH(OH)—CH_2(OH)$; $—(CH_2)—CH(COOH)—NH_2$;

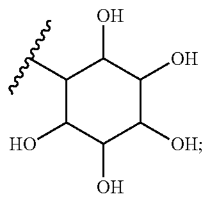

$R^2$ is —O—C(═O)—R; and

R is the same, and selected from $—(CH_2)_{14}—CH_3$; $—(CH_2)_{16}—CH_3$; $—(CH_2)_3—(CH═CH—CH_2)_4—(CH_2)_3—CH_3$; and $—(CH_2)_7—CH═CH—(CH_2)_7—CH_3$.

In a preferred embodiment of the method, the phospholipidic stabilizing agent is selected from the group comprising phospholipids with hydrophilic headgroup selected from phosphatidylethanolamine (PE), lysophosphatidylethanolamine (LPE), phosphatidylcholine (PC), lysophosphatidylcholine (LPC), phosphatidic acid (PA), lysophosphatidic acid (LPA), phosphatidylglycerol (PG), lysophosphatidylglycerol (LPG), phosphoinositide (PI), lysophosphoinositide (LPI), phosphatidylserine (PS), lysophosphatidylserine (LPS); and with lipophilic linear carbohydrate chains containing from 6 to 20 carbon atoms, preferably containing from 14 to 18 carbon atoms.

In a more preferred embodiment, the combination of stabilizing agents in step (a) comprises from 2 to 20 mol. % of the PEG-coupled phospholipid of general formula (I), from 0 to 20 mol. % of an anionic phospholipid, selected from the group comprising phospholipids with hydrophilic headgroup selected from phosphatidic acid (PA), lysophosphatidic acid (LPA), phosphatidylglycerol (PG), lysophosphatidylglycerol (LPG), phosphoinositide (PI), lysophosphoinositide (LPI), phosphatidylserine (PS), lysophosphatidylserine (LPS); and with lipophilic carbohydrate chains containing from 6 to 20 carbon atoms; and from 60 to 98 mol. % of a phospholipid, selected from the group comprising phospholipids with hydrophilic headgroup selected from phosphatidylethanolamine (PE), lysophosphatidylethanolamine (LPE), phosphatidylcholine (PC), lysophosphatidylcholine (LPC), and with lipophilic carbohydrate chains containing from 6 to 20 carbon atoms.

In yet a more preferred embodiment, the combination of stabilizing agents in step (a) comprises from 2 to 20 mol. % of PEG-coupled phospholipid of general formula (I), from 60 to 98 mol. % of phosphatidylcholine, and from 0 to 20 mol. % of phosphatidylglycerol, wherein the lipophilic carbohydrate chains of all the phospholipids contain from 14 to 18 carbon atoms.

In the most preffered embodiment, the combination of phospholipidic stabilizing agents comprises from 80 to 94 mol. % of dipalmitoylphosphatidylcholine (DPPC), from 2 to 10 mol. % of dipalmitoylphosphatidylglycerol (DPPG), and from 4 to 10 mol. % of PEG-coupled phospholipid of general formula (I), wherein R is $-(CH_2)_{14}-CH_3$; and n is in the range of from 40 to 80, most preferably n is 50 (MPEG-DMPE). Preferably, the combination of phospholipidic stabilizing agents comprises from 82 to 93 mol. % of DPPC, from 2 to 10 mol. % of DPPG, and from 5 to 8 mol. % of MPEG-DMPE. Most preferably, the molar ratio of DPPC:DPPG:MPEG-DMPE is 85:10:5.

Another object of the present invention is an aqueous pharmaceutical nanosuspension of API, comprising nanocrystalline API selected from the group comprising API, which have their intrinsic solubility in water of at most 50 mg/L, preferably at most 25 mg/L, (calculated according to Hou, T. J., Xia, K., Zhang, W., & Xu, X. J. (2004). ADME evaluation in drug discovery. 4. Prediction of aqueous solubility based on atom contribution approach. *Journal of chemical information and computer sciences,* 44(1), 266-275; implemented to ChemAxon solubility calculation plugin), and having log P of at least 4 (calculated according to Viswanadhan, V. N., Ghose, A. K., Revankar, G. R., & Robins, R. K. (1989). Atomic physicochemical parameters for three dimensional structure directed quantitative structure-activity relationships. 4. Additional parameters for hydrophobic and dispersive interactions and their application for an automated superposition of certain naturally occurring nucleoside antibiotics. *Journal of chemical information and computer sciences,* 29(3), 163-172; implemented in ChemAxon logP calculation plugin);

and a combination of at least two stabilizing agents, selected from the group of phospholipids containing lipophilic carbohydrate chains comprising from 6 to 20 carbon atoms;

wherein at least one of the stabilizing agents is selected from the group of PEG-coupled phospholipids of general formula (I), (I)

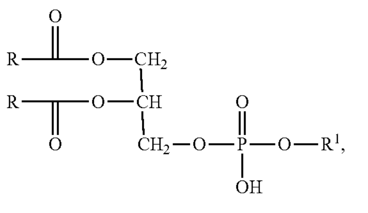

wherein R is independently selected from (C6 to C20) alkyl and (C6 to C20)alkenyl;

$R^1$ is

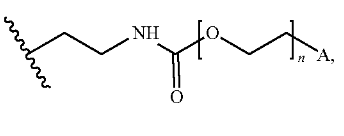

wherein n is an integer in the range of from 8 to 125 (corresponding to PEG molecular mass in the range of from 350 to 5000 g/mol); and wherein A is selected from the group comprising $-OH$, $-OCH_3$, $-NH_2$, $-NH-(C{=}O)-CH_2-CH_2-COOH$, $-NH-(C{=}O)-CH_2-CH_2-SH$; $-CH_2COOH$, $-N_3$, $-O-CH_2COOH$, $-CH_2CH({=}O)$;

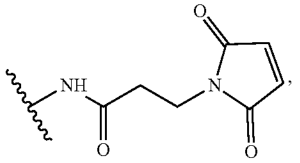

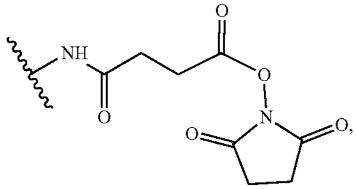

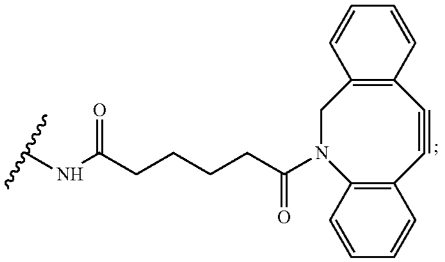

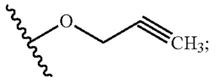

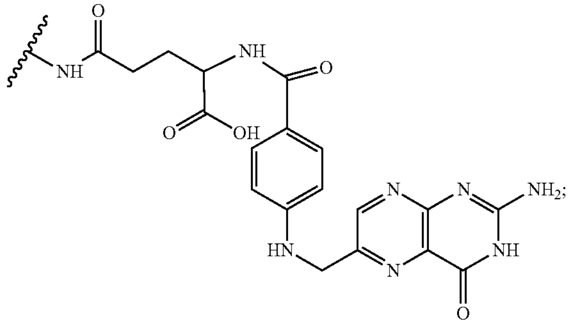

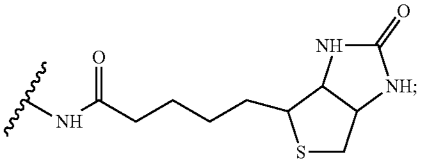

wherein the weight ratio of API to the stabilizing agent combination is at most 20:1, preferably the weight ratio of API to the stabilizing agent combination is in the range of from 10:1 to 1:1, more preferably 2:1 to 1:1, even more preferably from 3:2 to 1:1;

and wherein the molar ratio of the PEG-coupled phospholipids of general formula (I) to the other phospholipids is in the range of from 1:49 to 1:4, more preferably from 1:24 to 1:9, the most preferably from 1:19 to 2:23. This corresponds to the content of the PEG-coupled phospholipids of general formula (I) in the range of from 2 to 20 mol. %, more preferably from 4 to 10 mol. %, most preferably from 5 to 8 mol. %, related to the overall content of phospholipidic stabilizing agents;

and wherein the size of the API nanocrystals is at most 300 nm, determined using Dynamic Light Scattering (Microtrac NANO-flex, demineralized water, 20° C.), preferably at most 200 nm, more preferably in the range of from 1 to 200 nm.

The colloidal stability of the nanosuspension was confirmed by measuring particle size in a solution of a need (buffer, cell culture medium or other) using DLS (Microtrack NANO-flex, 10 mM phosphate buffered saline pH 7.4, 20° C.), wherein the obtained particle size did not exceed 1000 nm.

In one preferred embodiment, the aqueous pharmaceutical nanosuspension of API has concentration of nanocrystalline API in the range of from 10 mg/mL to 100 mg/mL, preferably from 15 mg/mL to 80 mg/mL, more preferably from 20 mg/mL to 70 mg/mL, the most preferably 60 mg/mL.

In one embodiment, API is selected from the group comprising curcumin, abiraterone acetate, ivacaftor, atorvastatin, candesartan cilexetil, and telmisartan.

In one preferred embodiment, the aqueous pharmaceutical nanosuspension of API, comprises nanocrystalline API selected from the group comprising API, which have their intrinsic solubility in water of at most 50 mg/L, preferably at most 25 mg/L, and having log P of at least 4;

and a combination of at least two stabilizing agents selected from the group of phospholipids, wherein the combination of stabilizing agents comprises from 2 to 20 mol. % of PEG-coupled phospholipid of general formula (I), from 60 to 98 mol. % of phosphatidylcholine, and from 0 to 20 mol. % of phosphatidylglycerol, wherein the lipophilic carbohydrate chains of all the phospholipids contain from 14 to 18 carbon atoms.

More preferably, the combination of phospholipidic stabilizing agents comprises from 80 to 94 mol. % of dipalmitoylphosphatidylcholine (DPPC), from 2 to 10 mol. % of dipalmitoylphosphatidylglycerol (DPPG), and from 4 to 10 mol. % of PEG-coupled phospholipid of general formula (I), wherein R is $—(CH_2)_{14}—CH_3$; and n is in the range of from 40 to 80, most preferably n is 50 (MPEG-DMPE). Preferably, the combination of phospholipidic stabilizing agents comprises from 82 to 93 mol. % of DPPC, from 2 to 10 mol. % of DPPG, and from 5 to 8 mol. % of MPEG-DMPE. Most preferably, the molar ratio of DPPC:DPPG:MPEG-DMPE is 85:10:5. Most preferably, MPEG-DMPE is MPEG2000-DMPE (molar mass of PEG is approximately 2000).

In one preferred embodiment, the size of the API nanocrystals is at most 200 nm, determined using Dynamic Light Scattering (Microtrac NANO-flex, demineralized water, 20° C.).

In a more preferred embodiment, the aqueous pharmaceutical nanosuspension comprises API selected from the group comprising curcumin, abiraterone acetate, ivacaftor, atorvastatin, candesartan cilexetil, and telmisartan, and a combination of at least two stabilizing agents, wherein at least one of the stabilizing agents is a phospholipidic stabilizing agent selected from the group comprising phospholipids containing lipophilic carbohydrate chains comprising from 12 to 18 carbon atoms; and hydrophilic head group comprising of PC, PG, and PE, and mixtures thereof; and at least one of the stabilizing agents is PEG-coupled phospholipid of general formula (I) as defined above;

wherein the concentration of API in the nanosuspension is in the range of from 10 mg/mL to 100 mg/mL, wherein the weight ratio of API to the combination of stabilizing agents is in the range of from 10:1 to 1:1; and wherein the weight ratio of the non-PEG-coupled phospholipidic stabilizing agent to PEG-coupled phospholipid is in the range of from 19:1 to 9:1.

In the most preferred embodiment, the aqueous pharmaceutical nanosuspension comprises API selected from the group comprising curcumin, abiraterone acetate, ivacaftor, atorvastatin, candesartan cilexetil, and telmisartan, in the concentration range of from 10 mg/mL to 100 mg/mL, and a combination of dipalmitoylphosphatidylcholine (DPPC), dipalmitoylphosphatidylglycerol (DPPG), and PEG-coupled phospholipid of general formula (I), wherein R is $—(CH_2)_{14}—CH_3$; and n is in the range of from 40 to 80, most preferably n is 50 (MPEG-DMPE), wherein the molar ratio of DPPC:DPPG:MPEG-DMPE is 85:10:5.

In particular, the aqueous pharmaceutical nanosuspension is obtainable by the method for preparing an aqueous nanosuspension of API described above, comprising the steps of:

(a) preparing an aqueous suspension comprising a crystalline API selected from the group comprising API having intrinsic solubility in water of at most 50 mg/L, preferably at most 25 mg/L, and having log P of at least 4;

and a combination of at least two stabilizing agents, selected from the group of phospholipids containing lipophilic carbohydrate chains comprising from 6 to 20 carbon atoms;

wherein at least one of the stabilizing agents is selected from the group of PEG-coupled phospholipids of general formula (I), defined above, wherein the weight ratio of API to the stabilizing agent combination in step (a) is at most 20:1, preferably the weight ratio of API to the stabilizing agent combination in step (a) is in the range of from 10:1 to 1:1, more preferably from 2:1 to 1:1, even more preferably from 3:2 to 1:1;

(b) placing milling balls, preferably $ZrO_2$ milling balls, even more preferably $ZrO_2$ milling balls with diameter in the range of from 0.2 to 0.7 mm, into the aqueous suspension from step (a); and (c) milling the aqueous suspension of step (b) to obtain nanocrystalline API suspension, wherein the size of the resulting API nanocrystals is at most 300 nm, determined using Dynamic Light Scattering (Microtrac NANO-flex, demineralized water, 20° C.).

Another object of the invention is a pharmaceutical composition, containing the aqueous pharmaceutical nanosuspension of API according to the present invention, and at least one pharmaceutically acceptable excipient. The pharmaceutically acceptable excipient may be selected from the group comprising, solvents, buffers, tonicity agents, glidants, fillers, lubricants, disintegrants, preservatives, antioxidants, chelating agents.

More particularly, glidants may be selected from colloidal anhydrous silica, talc and/or calcium silicate; fillers may be selected from microcrystalline silicified cellulose, microcrystalline cellulose, mannitol, lactose, starch and pregelatinized starch.

Lubricants may be selected from magnesium stearate, talc, calcium stearate and stearic acid.

Disintegrants may be selected from sodium croscarmellose, polyvinylpyrrolidon and sodium salt of carboxymethylstarch.

Solvents may be selected from water for injection, alcohol, benzyl benzoate, castor oil, dimethylacetamide, glycerin, polyethylene glycol, and soybean oil.

Buffers may be selected from citric acid monohydrate, glycine, maleic acid, methionine, sodium acetate, sodium citrate dihydrate, and sodium phosphate dibasic.

Tonicity agents may be selected from dextrose, mannitol, potassium chloride, sodium chloride, and propylene glycol.

Preservatives may be selected from citric acid monohydrate, benzalkonium chloride, benzoic acid, chlorobutanol, methylparaben, propylparaben, phenol, and sodium metabisulfite.

Antioxidants may be selected from ascorbic acid, butylated hydroxytoluene, methionine, citric acid monohydrate, methionine, and sodium metabisulfite.

Chelating agents may be selected from citric acid monohydrate, disodium edetate, edetate calcium disodium, and diethylenetriaminepentaacetic acid.

In one embodiment, the pharmaceutical composition is an oral dosage form, selected from tablets, coated tablets, pills, orally disintegrating tablets, capsules, powders and/or granules.

In one embodiment, the pharmaceutical composition is a parenteral dosage form.

In one embodiment, the pharmaceutical composition contains a dried pharmaceutical nanosuspension, prepared using the method according to the present invention, followed by a step of drying (water removal).

Another object of the invention is the use of the aqueous pharmaceutical nanosuspension of API in pharmaceutics, in particular for in vitro development, screening and testing of new natural or synthetic drug candidates or new drug forms of API.

Another object of the invention is the use of the combination of at least two stabilizing agents to stabilize aqueous nanosuspensions of low water soluble nanocrystalline compounds (having intrinsic solubility in water of at most 50 mg/L, preferably at most 25 mg/L, and having log P of at least 4, both calculated using the above described ChemAxon calculation plugins), preferably the low water soluble nanocrystalline compounds are pharmaceutically active ingredients, wherein the stabilizing agents are selected from the group of phospholipids containing lipophilic carbohydrate chains comprising from 6 to 20 carbon atoms; preferably the lipophilic carbohydrate chains are independently selected from $-(CH_2)_{14}-CH_3$; $-(CH_2)_{16}-CH_3$; $-(CH_2)_3-(CH{=}CH-CH_2)_4-(CH_2)_3-CH_3$; and $-(CH_2)_7-CH{=}CH-(CH_2)_7-CH_3$;

and wherein at least one of the stabilizing agents is selected from the group of PEG-coupled phospholipids of general formula (I), defined above;

and wherein the content of the PEG-coupled phospholipids of general formula (I) is in the range of from 2 to 20 mol. %, more preferably from 4 to 10 mol. %, most preferably from 5 to 8 mol. %, related to the overall content of phospholipidic stabilizing agents in the combination.

Preferably, the combination of at least two stabilizing agents contains from 2 to 20 mol. % of the PEG-coupled phospholipid of general formula (I), and from 80 to 98 mol. % of the non-PEG coupled phospholipid of general formula (II), as defined above, related to the overall content of phospholipidic stabilizing agents in the combination.

EXAMPLES

Materials and Methods

Figure 1:
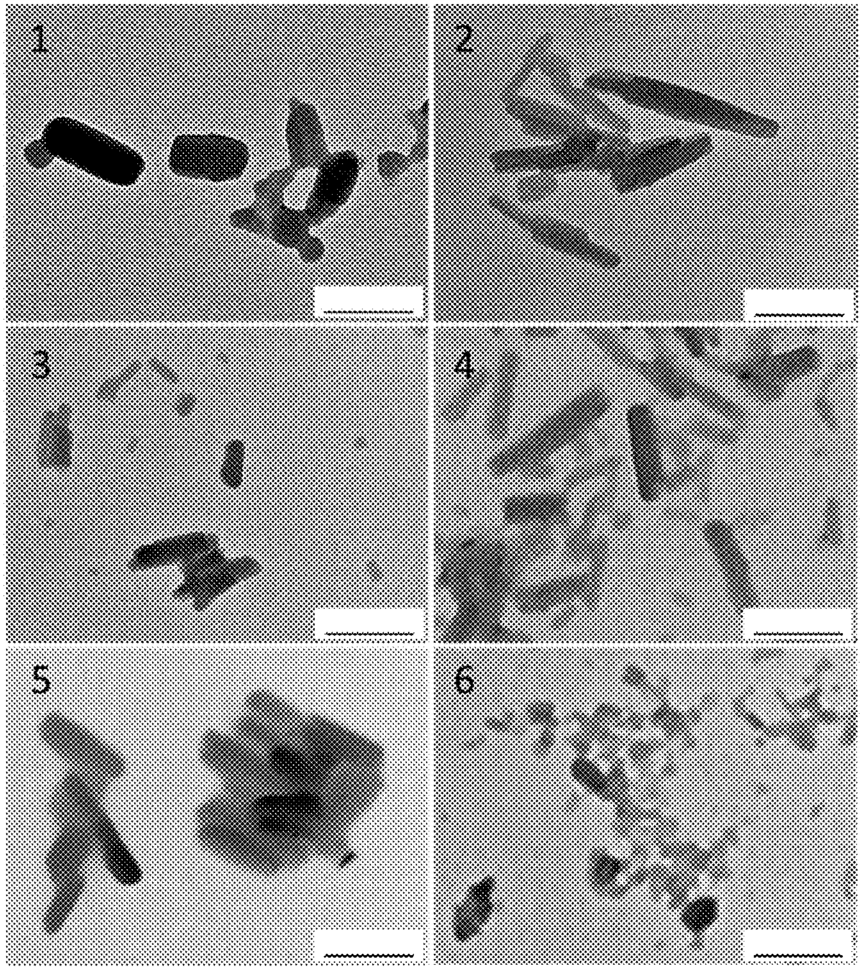
FIG. 1 TEM images of nanocrystals stabilized with phospholipidic mixture (85 mol % of DPPC, 10 mol % of DPPG, 5 mol % of MPEG2000-DMPE). 1: Abiraterone acetate, 2: Telmisartan, 3: Ivacaftor, 4: Candesartan, 5: Atorvastatin, 6: Curcumin. Scale bar represents 200 nm.

The following chemicals were used: dipalmitoylphosphatidylcholine (DPPC) and 1.2-dimyristoyl-sn-glycero-3-phosphoethanolamine conjugated polyethylene glycol 2000 (MPEG-DMPE) from Corden Pharma, dipalmitoylphosphatidylglycerol (DPPG) from Sigma-Aldrich, methanol from Penta. Demineralized water (conductivity <1 μS/cm) was produced by the Aqual 25 ionex device (Aqual, Czech Republic). Curcumin (6) (ASB-00003925-005, 99.9% purity) was purchased from Chromadex, California. $ZrO_2$ milling balls (0.5 mm) were purchased from Ginzel, Czech Republic. Abiraterone acetate (1), Telmisartan (2), Ivacaftor (3), Candesartan cilexetil (4), and Atorvastatin (5) were purchased from Merck.

Cells and Media

HT-29 (human, epithelial, colon, disease: colorectal adenocarcinoma) and J774A.1 (mouse, macrophage, disease: reticulum cell sarcoma) cell lines were cultured in Dulbecco's Modified Eagle's Medium-high glucose (DMEM; Merck D6429) supplemented with 10% heat-inactivated fetal bovine serum (Merck F7524) and 1% mix of antibiotics and antimycotics Anti-Anti (Merck A5955). MRC-5 primary cells (human, fibroblast, lung, disease: normal) were cultured in StableCell™ MEM medium (MEM; Merck M0446) supplemented with 10% heat-inactivated fetal bovine serum.

The cells were cultured at 37° C. in a 5% $CO_2$ atmosphere until 70-80% confluency and then harvested by either scraping (J774A.1) or trypsinization (HT-29, MRC-5). For the nanocrystal stability, cytotoxicity, phagocytosis, and effect on the proliferation, the cells were further washed and/or analyzed in phosphate-buffered saline (PBS; 10 mM, pH 7.4, sterile), DMEM, or MEM medium. The cells viability was measured using Cell Counting Kit-8 (CCK-8, Merck 96992), which uses bioreduction of WST-8 (2-(2-methoxy-4-nitrophenyl)-3-(4-nitrophenyl)-5-(2,4-disulfophenyl)-2H-tetrazolium, monosodium salt) into a water-soluble yellow formazan dye (absorbance measurement at 450 nm). All viability tests and confocal microscopy experiments were repeated at least three times, where the obtained data were always in agreement.

Cell Culturing

HT-29 (human, epithelial, colon, disease: colorectal adenocarcinoma) and J774A.1 (mouse, macrophage, disease: reticulum cell sarcoma) cell lines were cultured in Dulbecco's Modified Eagle's Medium-high glucose (DMEM; Merck D6429) supplemented with 10% heat-inactivated fetal bovine serum (Merck F7524) and 1% mix of antibiotics and antimycotics Anti—Anti (Merck A5955). MRC-5 primary cells (human, fibroblast, lung, disease: normal) were cultured in StableCell™ MEM medium (MEM; Merck M0446) supplemented with 10% heat-inactivated fetal bovine serum.

The cells were cultured at 37° C. in a 5% $CO_2$ atmosphere until 70-80% confluency and then harvested by either scraping (J774A.1) or trypsinization (HT-29, MRC-5). For the nanocrystal stability, cytotoxicity, phagocytosis, and effect on the proliferation, the cells were further washed and/or analyzed in phosphate-buffered saline (PBS; 10 mM, pH 7.4, sterile), DMEM, or MEM medium. The cells viability was measured using Cell Counting Kit-8 (CCK-8, Merck 96992), which uses bioreduction of WST-8 (2-(2-methoxy-4-nitrophenyl)-3-(4-nitrophenyl)-5-(2,4-disulfophenyl)-2H-tetrazolium, monosodium salt) into a water-soluble yellow formazan dye (absorbance measurement at 450 nm). All viability tests and confocal microscopy experiments were repeated at least three times, where the obtained data were always in agreement.

Example 1: Preparation, Characterization and Colloidal Stability of Nanosuspensions

1.1 Nanosuspensions of Various APIs With Phospholipidic Stabilization

1.1.1 Preparation of API Nanosuspension

As a standard procedure, all samples were prepared as follows: 60 mg of API was milled together with 40 mg of a combination of stabilizers (DPPC:DPPG:MPEG2000-DMPE in molar ratio 85:10:5). The milling was performed in a 25 mL amber vial filled with one mL of distilled water using 5 g of $ZrO_2$ milling balls with diameter of 0.4-0.5 mm and magnetic cross stirrer (8×25 mm, 600 rpm). The milling was performed for 24 hours at room temperature and after that the suspensions were stored in fridge until further use. The APIs used for the preparation of nanosuspensions are listed in Table 1. The intrinsic solubility in water of API was calculated according to Hou, T. J., Xia, K., Zhang, & Xu, X. J. (2004). ADME evaluation in drug discovery. 4. Prediction of aqueous solubility based on atom contribution approach. *Journal of chemical information and computer sciences,* 44(1), 266-275; implemented to ChemAxon solubility calculation plugin.

The partition coefficient of lipophilicity (log P) of API was calculated according to Viswanadhan, V. N., Ghose, A. K., Revankar, G. R., & Robins, R. K. (1989). Atomic physicochemical parameters for three dimensional structure directed quantitative structure-activity relationships. 4. Additional parameters for hydrophobic and dispersive interactions and their application for art automated superposition of certain naturally occurring nucleoside antibiotics. *Journal of chemical information and computer sciences,* 29(3), 163-172; implemented in ChemAxon logP calculation plugin.

Figure 2:
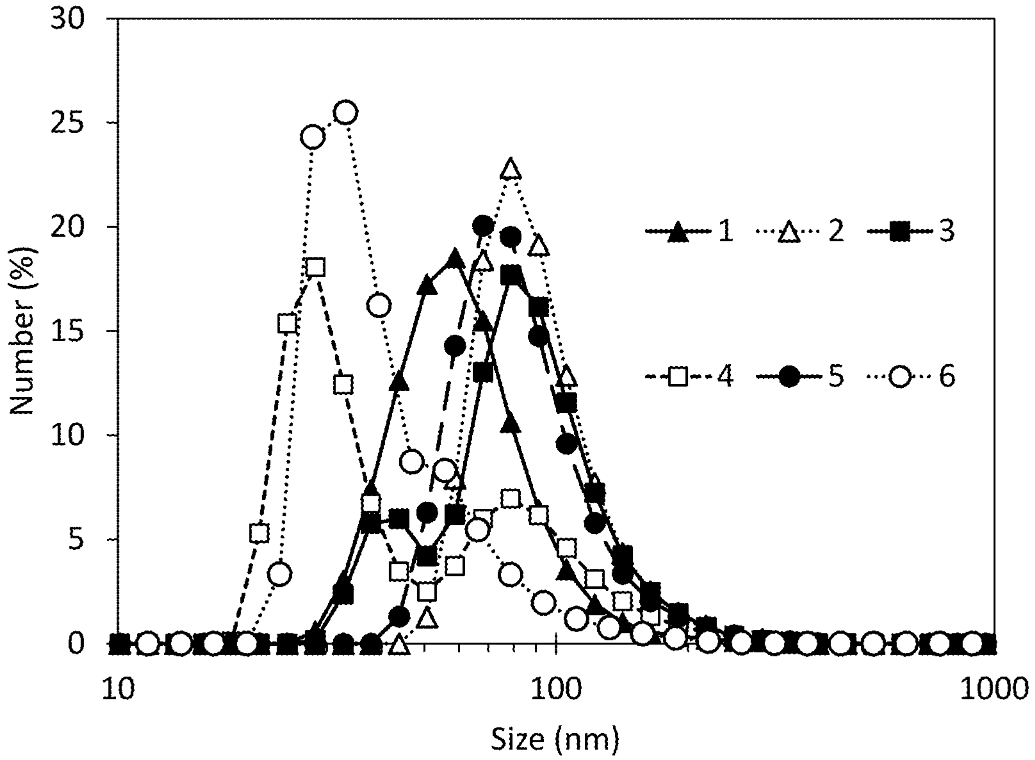
FIG. 2 Particle size distribution (number based) of API nanosuspensions, measured by DLS in demineralized water. Sterile-filtered nanocrystals stabilized with phospholipidic mixture (85 mol % of DPPC, 10 mol % of DPPG, 5 mol % of MPEG2000-DMPE) are labelled as follows: 1: Abiraterone acetate, 2: Telmisartan, 3: Ivacaftor, 4: Candesartan, 5: Atorvastatin, 6: Curcumin FIG. 3A ATR-FTIR spectra of phospholipids DPPC, FIG. 3B DPPG, and FIG. 3C MPEG2000-DMPE used for the stabilization of nanocrystals.
Figure 3A:
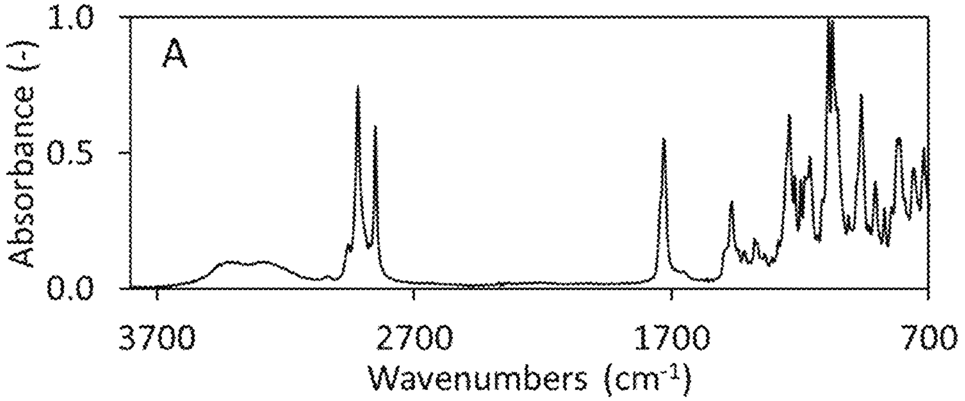
Figure 3B:
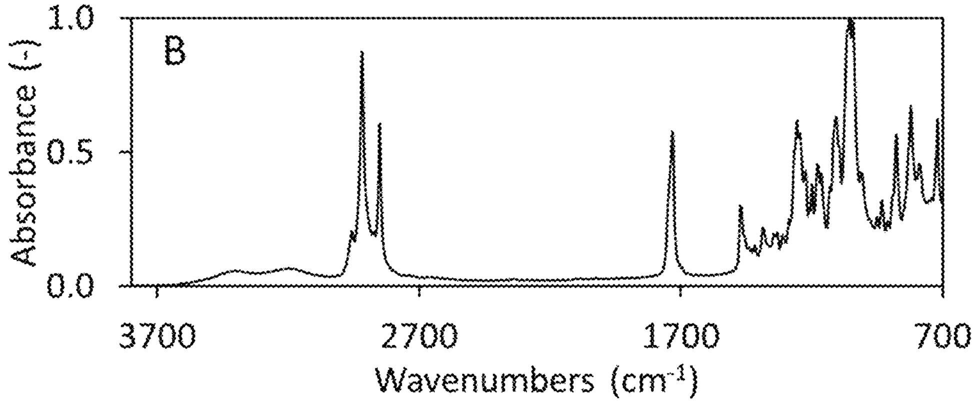
Figure 3C:
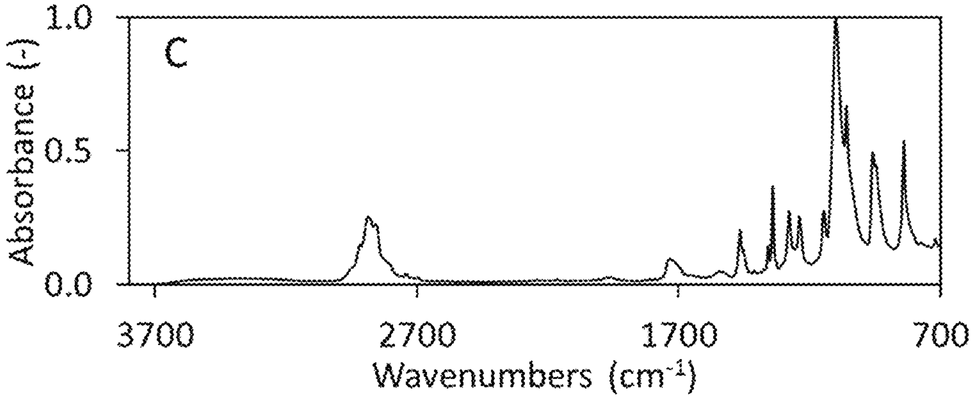
Figure 4A:
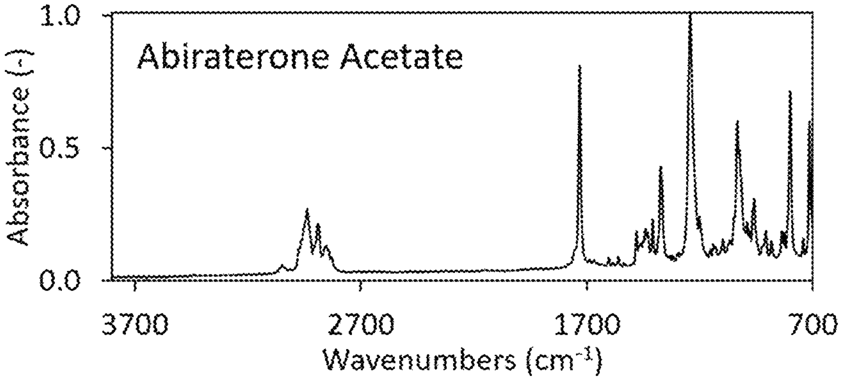
FIGS. 4A-4B ATR-FTIR spectra of abiraterone acetate (top) and abiraterone acetate nanocrystals stabilized with phospholipidic mixture (85 mol % of DPPC, 10 mol % of DPPG, 5 mol % of MPEG2000-DMPE) (bottom). The arrows indicate absorption bands confirming presence of the stabilizer in the spectrum of nanocrystals. All other absorption bands in the spectrum of nanocrystals correspond to the API.
Figure 4B:
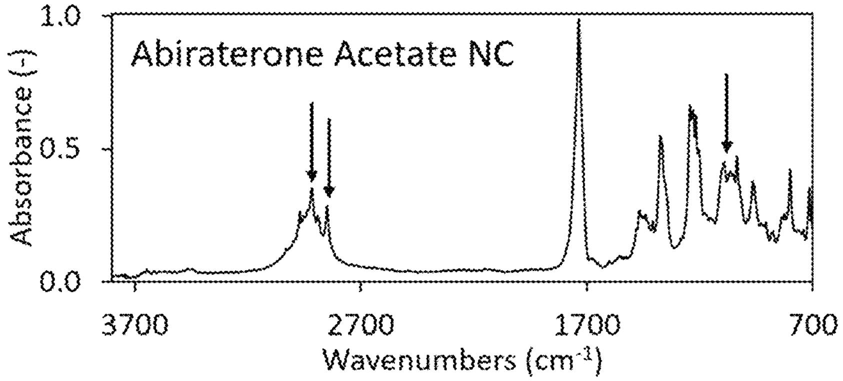
Figure 5A:
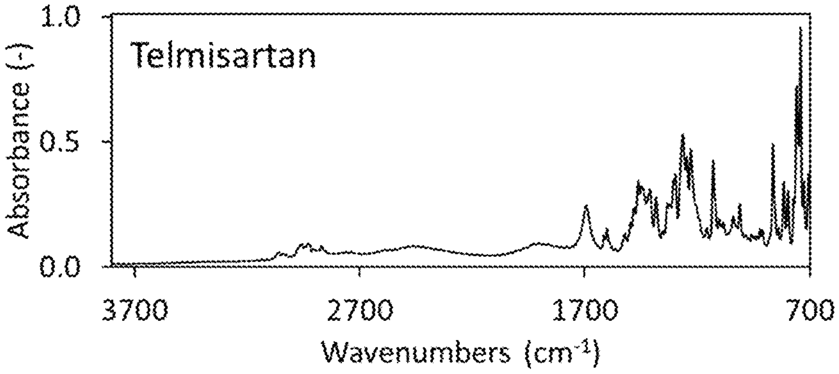
FIGS. 5A-5B ATR-FTIR spectra of telmisartan (top) and telmisartan nanocrystals stabilized with phospholipidic mixture (85 mol % of DPPC, 10 mol % of DPPG, 5 mol % of MPEG2000-DMPE) (bottom). The arrows indicate absorption bands confirming presence of the stabilizer in the spectrum of nanocrystals. All other absorption bands in the spectrum of nanocrystals correspond to the API.
Figure 5B:
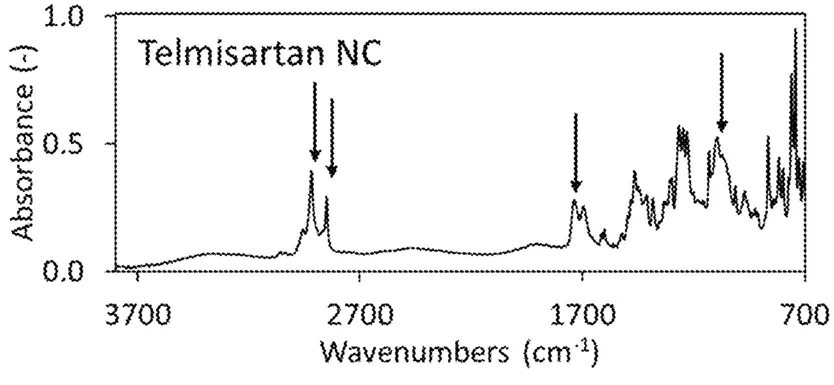
Figure 6A:
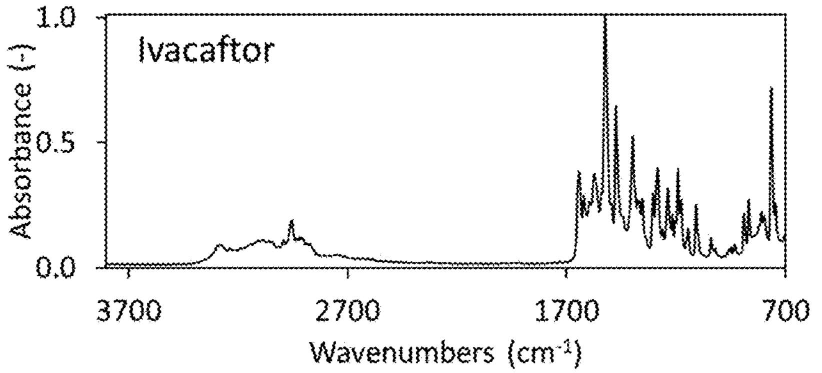
FIGS. 6A-6B ATR-FTIR spectra of ivacaftor (top) and ivacaftor nanocrystals stabilized with phospholipidic mixture (85 mol % of DPPC, 10 mol % of DPPG, 5 mol % of MPEG2000-DMPE) (bottom). The arrows indicate absorption bands confirming presence of the stabilizer in the spectrum of nanocrystals. All other absorption bands in the spectrum of nanocrystals correspond to the API.
Figure 6B:
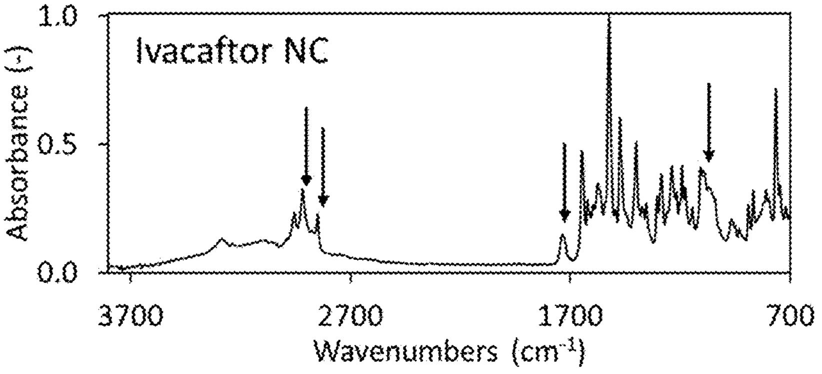
Figure 7A:
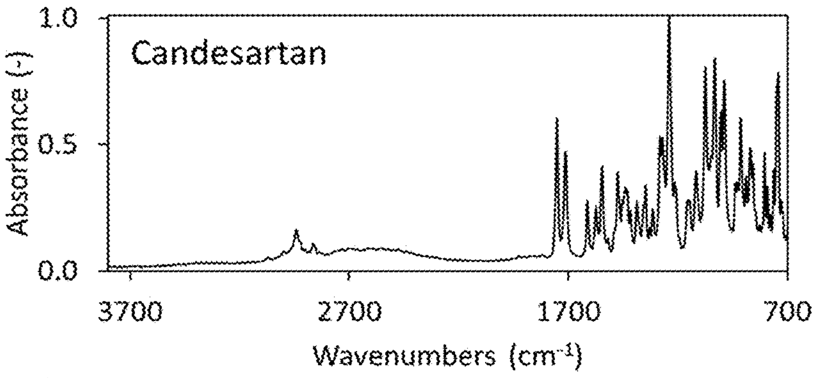
FIGS. 7A-7B ATR-FTIR spectra of candesartan cilexetil (top) and candesartan cilexetil nanocrystals stabilized with phospholipidic mixture (85 mol % of DPPC, 10 mol % of DPPG, 5 mol % of MPEG2000-DMPE) (bottom). The arrows indicate absorption bands confirming presence of the stabilizer in the spectrum of nanocrystals. All other absorption bands in the spectrum of nanocrystals correspond to the API.
Figure 7B:
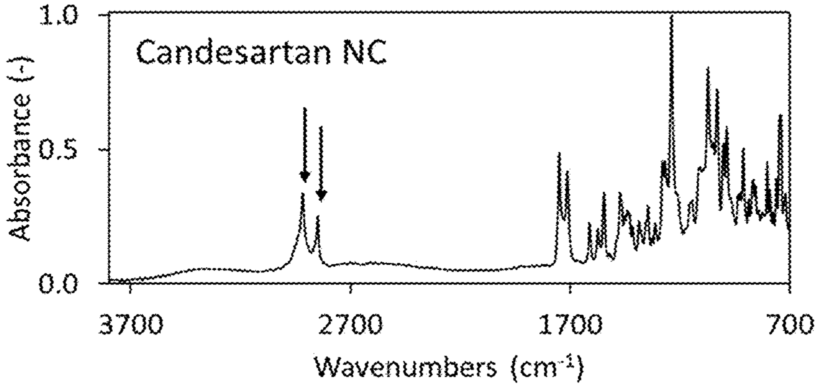
Figure 8A:
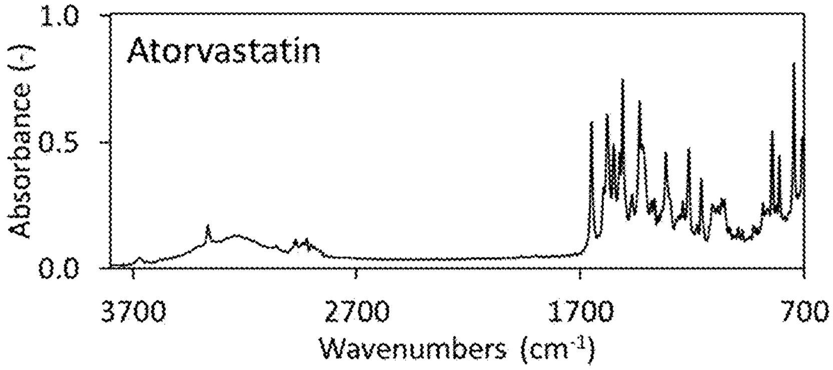
FIGS. 8A-8B ATR-FTIR spectra of atorvastatin (top) and atorvastatin nanocrystals stabilized with phospholipidic mixture (85 mol % of DPPC, 10 mol % of DPPG, 5 mol % of MPEG2000-DMPE) (bottom). The arrows indicate absorption bands confirming presence of the stabilizer in the spectrum of nanocrystals. All other absorption bands in the spectrum of nanocrystals correspond to the API.
Figure 8B:
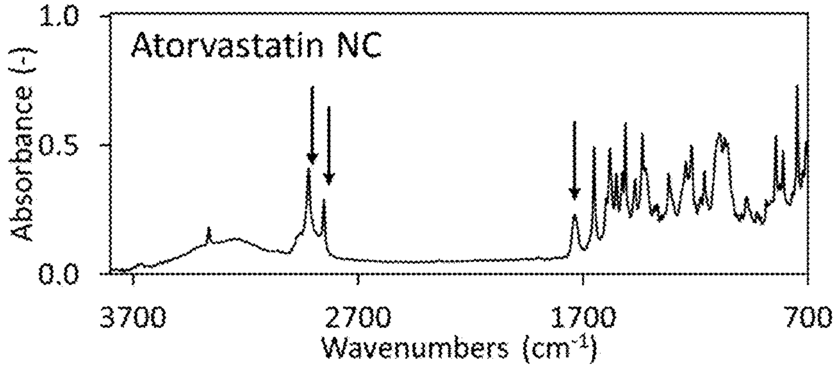
Figure 9A:
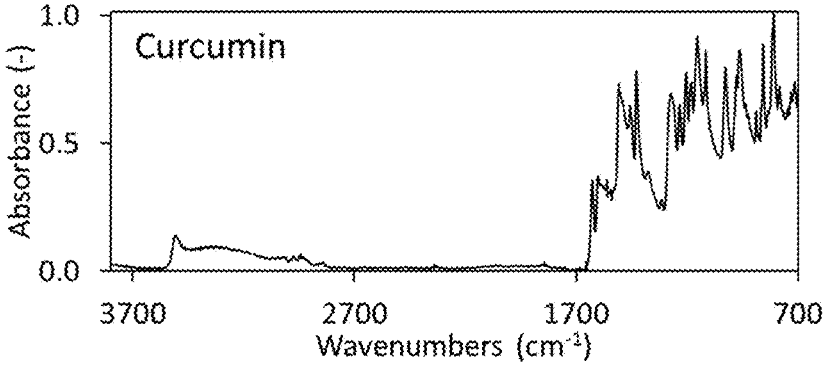
FIGS. 9A-9B ATR-FTIR spectra of curcumin (top) and curcumin nanocrystals stabilized with phospholipidic mixture (85 mol % of DPPC, 10 mol % of DPPG, 5 mol % of MPEG2000-DMPE) (bottom). The arrows indicate absorption bands confirming presence of the stabilizer in the spectrum of nanocrystals. All other absorption bands in the spectrum of nanocrystals correspond to the API.
Figure 9B:
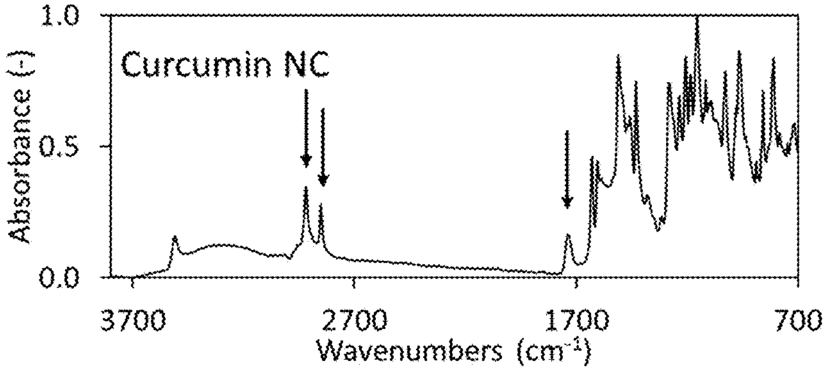
Figure 10:
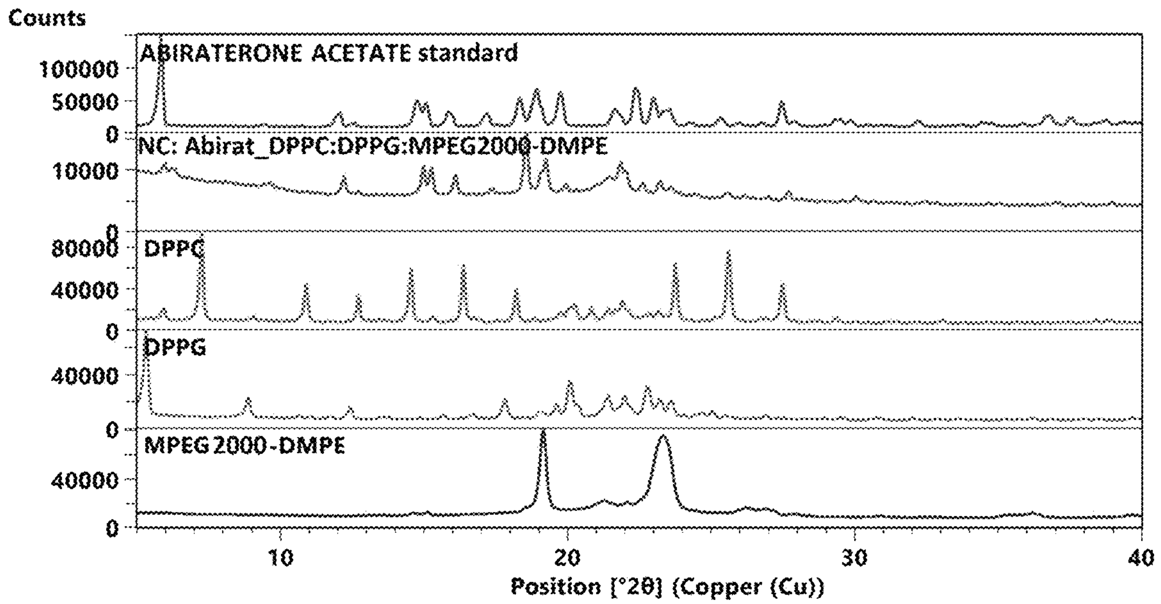
FIG. 10 XRD analysis of abiraterone acetate nanocrystals stabilized with phospholipidic mixture (85 mol % of DPPC, 10 mol % of DPPG, 5 mol % of MPEG2000-DMPE) confirming crystalline state of API in the nanocrystalline product of the milling No presence of the crystalline stabilizers was detected. Small amount of the crystalline phase was not identified.
Figure 11:
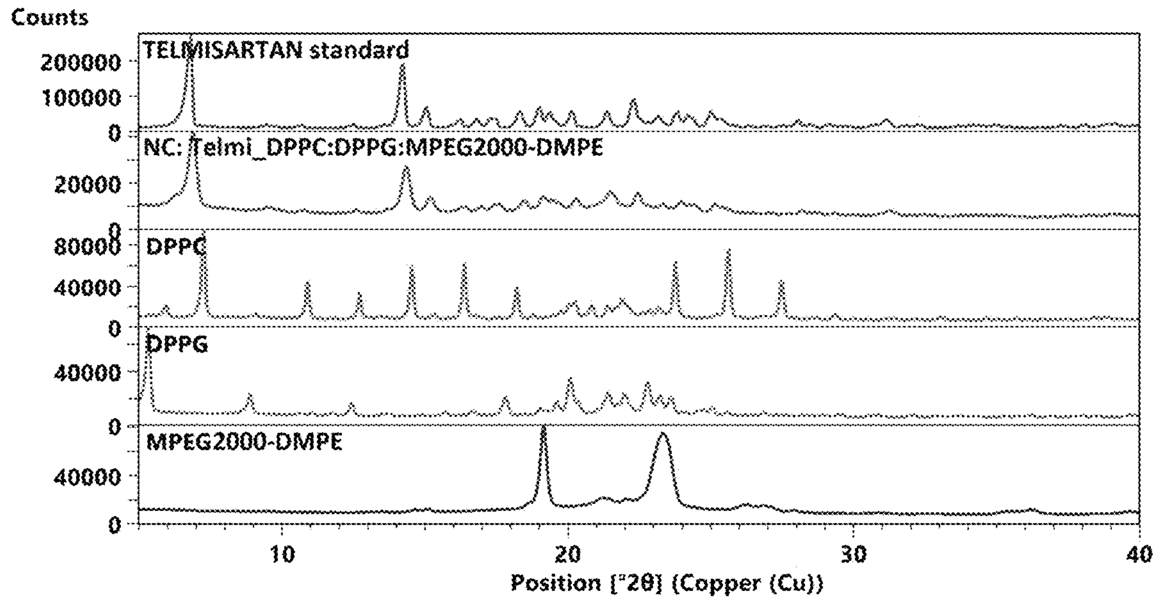
FIG. 11 XRD analysis of telmisartan nanocrystals stabilized with phospholipidic mixture (85 mol % of DPPC, 10 mol % of DPPG, 5 mol % of MPEG2000-DMPE) confirming crystalline state of API in the nanocrystalline product of the milling No presence of the crystalline stabilizers was detected. Detected crystalline phase fully corresponds to telmisartan.
Figure 12:
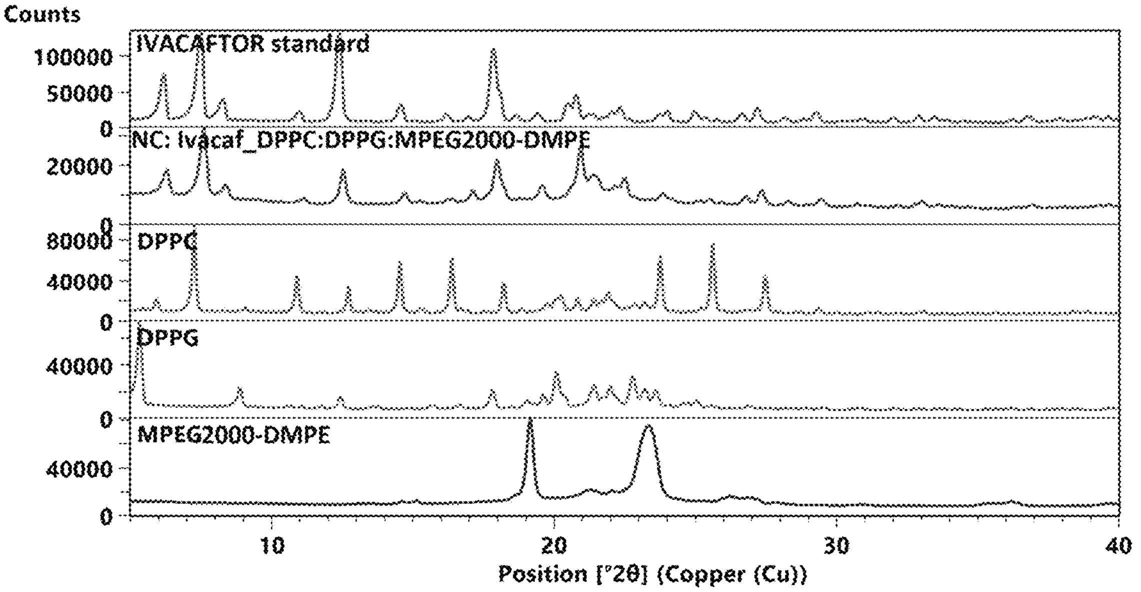
FIG. 12 XRD analysis of ivacaftor nanocrystals stabilized with phospholipidic mixture (85 mol % of DPPC, 10 mol % of DPPG, 5 mol % of MPEG2000-DMPE) confirming crystalline state of API in the nanocrystalline product of the milling No presence of the crystalline stabilizers was detected. Detected crystalline phase fully corresponds to ivacaftor.
Figure 13:
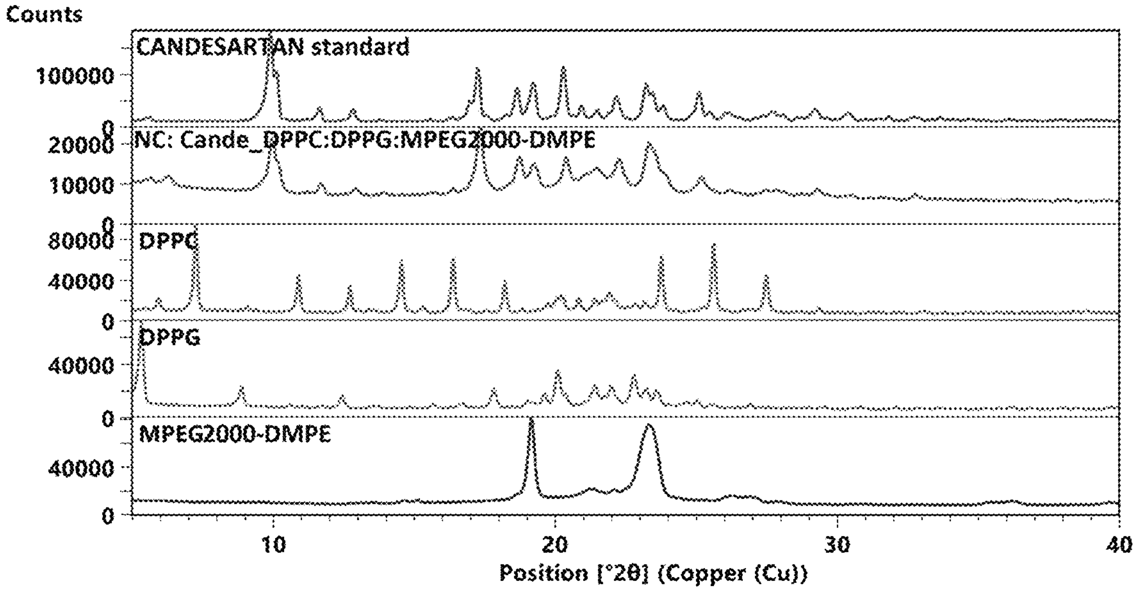
FIG. 13 XRD analysis of candesartan cilexetil nanocrystals stabilized with phospholipidic mixture (85 mol % of DPPC, 10 mol % of DPPG, 5 mol % of MPEG2000-DMPE) confirming crystalline state of API in the nanocrystalline product of the milling No presence of the crystalline stabilizers was detected. Small amount of the crystalline phase was not identified.
Figure 14:
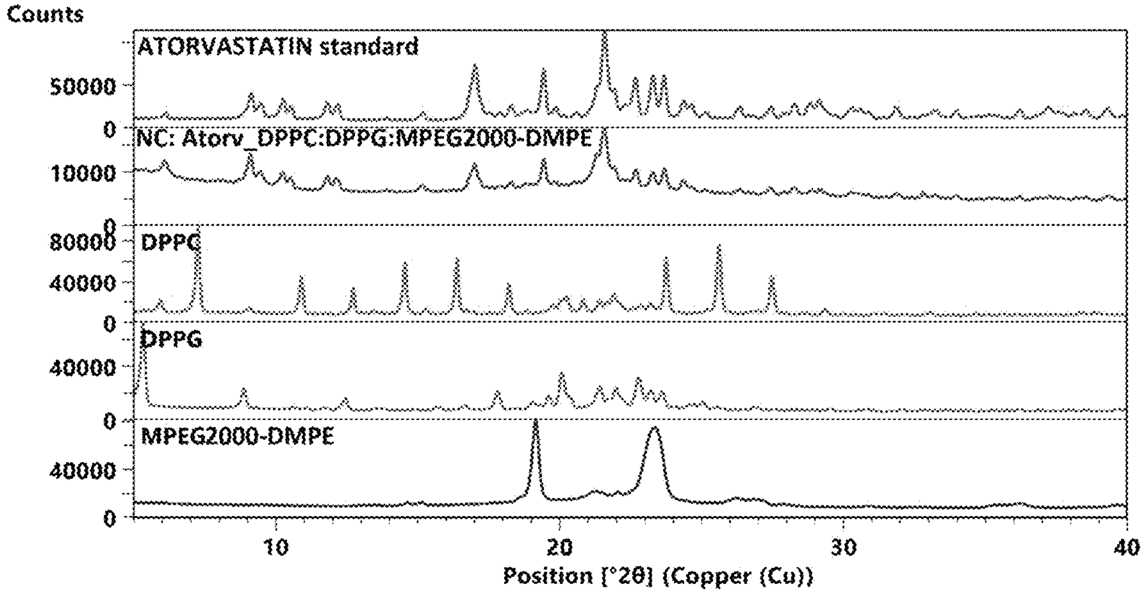
FIG. 14 XRD analysis of atorvastatin nanocrystals stabilized with phospholipidic mixture (85 mol % of DPPC, 10 mol % of DPPG, 5 mol % of MPEG2000-DMPE) confirming crystalline state of API in the nanocrystalline product of the milling No presence of the crystalline stabilizers was detected. Detected crystalline phase fully corresponds to atorvastatin.
Figure 15:
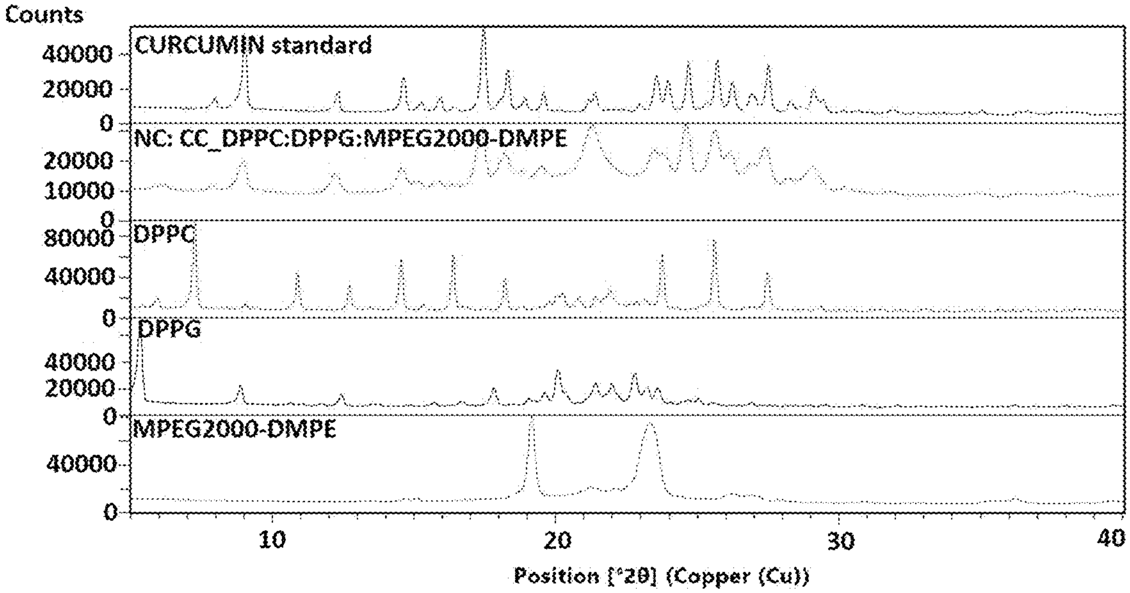
FIG. 15 XRD analysis of curcumin nanocrystals stabilized with phospholipidic mixture (85 mol % of DPPC, 10 mol % of DPPG, 5 mol % of MPEG2000-DMPE) confirming crystalline state of API in the nanocrystalline product of the milling No presence of the crystalline stabilizers was detected. Detected crystalline phase fully corresponds to curcumin.
Figure 16:
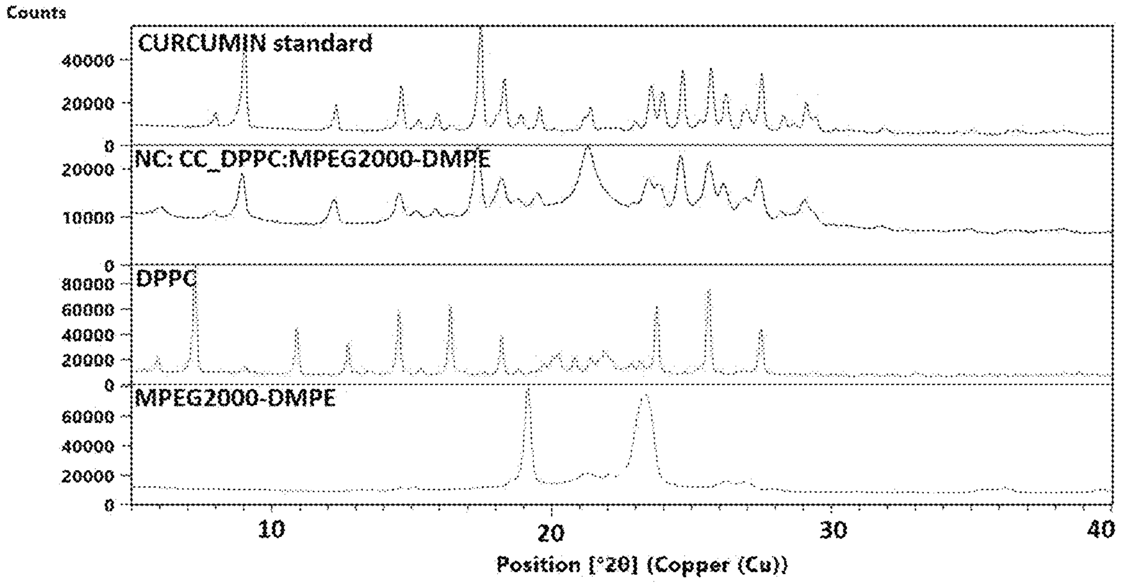
FIG. 16 XRD analysis of curcumin nanocrystals stabilized with phospholipidic mixture (95 mol % of DPPC, 5 mol % of MPEG2000-DMPE) confirming crystalline state of API in the nanocrystalline product of the milling. No presence of the crystalline stabilizers was detected. Detected crystalline phase fully corresponds to curcumin.

Table 2 summarizes different API:Stabilizer ratios used for the milling and resulting nanocrystals sizes measured by DLS in a demineralized water as described above. The particle size distributions of nanocrystal suspensions stabilized with phospholipidic mixture (85% DPPC, 10% DPPG, 5% MPEG2000-DMPE) are shown in FIG. 2.

TABLE 1

List of Tested API and their characteristics.

| Sample no. | API | Log P | Intrinsic solubility in water (mg/L) |
|---|---|---|---|
| 1 | Abiraterone acetate | 4.4 | 0.45 |
| 2 | Telmisartan | 7.8 | 0.005 |
| 3 | Ivacaftor | 5.7 | 0.11 |
| 4 | Candesartan cilexetil | 5.3 | 0.06 |
| 5 | Atorvastatin | 5.4 | 0.05 |
| 6 | Curcumin | 4.85 | 24.31 |

TABLE 2

Different API:Stabilizer ratios and resulting padticle size by DLS (in demineralized water).

| API (60 mg) | Stabilizer mass (mg) | DPPC % | DPPG % | MPEG2000-DMPE % | Number-mean particle size (nm) |
|---|---|---|---|---|---|
| — | 40 | 85 | 10 | 5 | See Table 4 |
| Curcumin | 40 | 95 | 0 | 5 | 90 ± 25 |
| Ivacaftor | 30 | 85 | 10 | 5 | 125 ± 45 |
| Ivacaftor | 20 | 85 | 10 | 5 | 91 ± 36 |
| Ivacaftor | 10 | 85 | 10 | 5 | 152 ± 42 |

1.1.2 Characterization Methods

Characterization of API nanocrystals was done by measuring their size using Dynamic Light Scattering (DLS, Microtrac NANO-flex with 180° heterodyne backscattering, suitable for fluorescent samples) using a 20 μL droplet of diluted suspension. Particle size distribution of input API crystals was measured by Static Light Scattering (SLS, Horiba Partica LA 950 S2) and Scanning Electron Microscopy (SEM; Jeol JCM 5700). The nanocrystal samples were analyzed by Transmission Electron Microscopy (TEM; Jeol-JEM1010). The TEM data are shown in FIG. 1. The scale bar represents 200 nm.

Attenuated Total Reflection (ATR) Fourier-transform infrared (FTIR) spectroscopy using Nicolet iZ10 spectrometer with ZnSe crystal was used to measure spectra of prepared and freeze-dried nanocrystals. The spectral resolution was 4 $cm^{-1}$, and the spectra were collected as 128 co-added scans. The results of FTIR are shown in FIG. 3-FIG. 9.

The X-ray diffraction (XRD) analysis was performed using PANalytical X'Pert PRO and software HighScore Plus in order to confirm the crystallinity of API in all samples and to confirm that there is no crystalline phase of the stabilizers present, which would otherwise indicate that the stabilizers recrystallize. XRD data are shown in FIG. 10-FIG. 16.

1.1.3 API Quantification in Sterile Filtered Nanosuspension and Colloidal Stability The nanocrystal suspensions were diluted to approximately 10 mg/mL (or 1 mg/mL in case of curcumin) in demineralized water, sterile-filtered (<200 nm) and the API content was quantified after dissolving 10 μL of the API nanocrystalline suspension in 1 mL of methanol (and further diluted, if necessary to fall into the absorbance range of the calibration). The quantification was done by UV-vis spectrophotometry. All stock solutions of API in methanol were prepared as three separate samples, from which the corresponding dilutions were prepared (therefore each calibration point was composed of three separately prepared solutions). The measured absorbance values at the absorption maximum used for the calibration curve preparation were in range of 0.2-1.5 and each calibration curve consisted of at least five concentration points. Table 3 shows the constructed calibration curve equations used for the quantification purposes and the measured concentrations of the nanosuspensions.

The colloidal stability, in means of particle size preservation when compared to the demineralized water, was measured by DLS in phosphate buffered saline pH 7.4 (10 mM). It was previously observed that the presence of salts has the strongest impact on the stability decrease, whereas the presence of proteins (for example serum in the cell culture medium) improves the nanocrystal stability. Therefore, the stability in PBS was measured as a limit case where the worst results can be expected. The results of the DLS measurements in both demineralized water (original solvent) and PBS pH 7.4 (physiological) are summarized in Table 4. No significant aggregation or sedimentation was observed. In case of telmisartan there was an increase in the mean diameter detected when measured in PBS, which indicates that these nanocrystals have lower stability in PBS than in demineralized water; the resulting mean particle diameter however did not exceed 400 nm and therefore such nanocrystals can be used for in vitro testing.

TABLE 3

Calibration curve parameters for API quantification and API concentrations in the suspensions after the sterile filtration. The suspensions were diluted prior the filtration.

| Sample | $\lambda_{max}$ (nm) | Calibration equation; $R^2$ y = c (μg/mL); x = absorbance at $\lambda_{max}$ | API content after sterile-filtration [mg/mL] |
|---|---|---|---|
| Abirat | 257 | y = 40.057x + 0.216; $R^2$ = 0.9995 | 1.26 ± 0.04 |
| Telmi | 299 | y = 21.487x + 0.170; $R^2$ = 0.9994 | 7.31 ± 0.41 |
| Ivacaf | 312 | y = 22.881x + 0.194; $R^2$ = 0.9991 | 5.01 ± 0.12 |
| Cande | 257 | y = 37.484x + 0.222; $R^2$ = 0.9994 | 5.78 ± 0.23 |
| Atorv | 249 | y = 27.243x + 0.260; $R^2$ = 0.9990 | 1.88 ± 0.29 |
| CC | 427 | y = 5.8116x + 0.0024; $R^2$ = 0.9996 | 0.56 ± 0.02 |

TABLE 4

Number mean particle size in demineralized water and phosphate buffered saline (PBS) pH 7.4; the combination of stabilizers used in all samples was DPPC:DPPG:MPEG2000-DMPE in molar ratio 85:10:5.

| Sample | Nanoparticle size in water [nm] | Nanoparticle size in PBS [nm] |
|---|---|---|
| Abirat | 64 ± 25 | 77 ± 30 |
| Telmi | 93 ± 34 | 383 ± 170 |
| Ivacaf | 97 ± 35 | 92 ± 33 |
| Cande | 84 ± 36 | 115 ± 44 |
| Atorv | 102 ± 14 | 35 ± 14 |
| CC | 54 ± 15 | 67 ± 17 |

1.2 Preparation, Characterization, and Stability of Curcumin Nanocrystals With Various Stabilizers Seven types of curcumin nanocrystals with different stabilizers were prepared by wet milling in demineralized water according to Example 1.1.1. Preparation of API nanosuspension. The composition of the stabilizers and their ratios are summarized in Table 5.

TABLE 5

Composition od curcumin nanocrystal samples woth different stabilizer. Each sample was prepared form 60 mg of curcumin and the amount of the stabilizer as listed below.

| | Stabilizer composition | Stabilizer:Curcumin (by mass) |
|---|---|---|
| 1 | Tween 80 | 1:3 |
| 2 | HPMC + SDS | 1:12 + 1:30 |
| 3 | SDS | 2:3 |
| 4 | Poloxamer P188 | 1:2 |
| 5 | DPPC:MPEG2000-DMPE (95:5) | 2:3 |
| 6 | DPPC:DPPG:MPEG2000-DMPE (85:10:5) | 2:3 |
| 7 | HPMC + DPPG | 1:12 + 1:30 |

Figure 17:
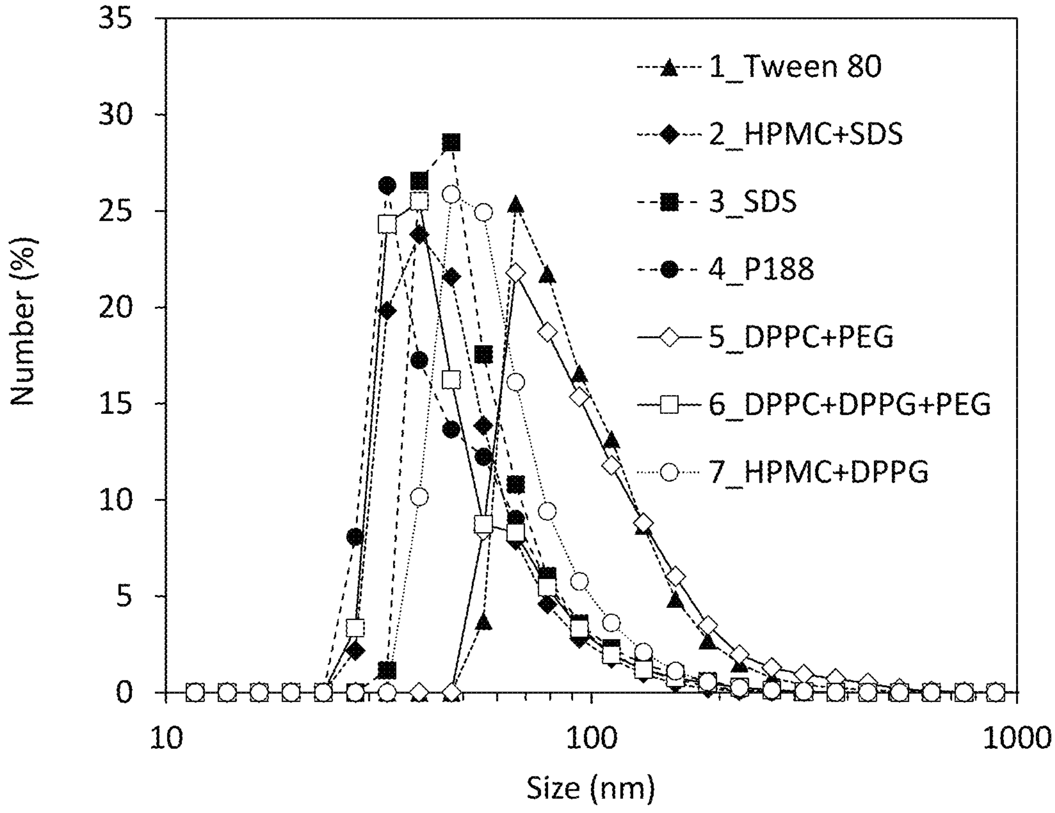
FIG. 17 Particle size distribution by DLS of curcumin nanocrystals with different stabilizations (after sterile filtration, in demineralized water).

Curcumin nanocrystals after the milling and sterile filtration were analyzed by dynamic light scattering (Microtrac NANO-flex, in demineralized water, 20° C.) and the size distributions are shown in FIG. 17. The DLS analysis revealed that the average diameters of the nanocrystals ranged from 40 to 90 nanometers (by number). The exact values of mean diameters together with the curcumin concentrations reached after the sterile filtration (quantified by UV-vis, see Table 3) are summarized in Table 6.

TABLE 6

Curcumin concentration (from UV-vis) after sterile-filtration and number-mean particle diameter (from DLS) of sterile-filtered curcumin nanocrystal samples (<200 nm) in demineralized water. The suspensions obtained from milling (60 mg/mL) were diluted 6-times prior to the filtration.

| Curcumin NC type | Curcumin concentration (μg/mL) | Number-mean diameter in water (nm) |
|---|---|---|
| 1_Tween 80 | 76 | 84 ± 26 |
| 2_HPMC + SDS | 830 | 43 ± 13 |
| 3_SDS | 781 | 49 ± 13 |
| 4_P188 | 793 | 43 ± 16 |
| 5_DPPC:MPEG2000-DMPE (95:5) | 381 | 90 ± 32 |
| 6_DPPC:DPPG:MPEG2000-DMPE (85:10:5) | 484 | 44 ± 15 |
| 7_HPMC_DPPG | 560 | 54 ± 15 |

Figure 18:
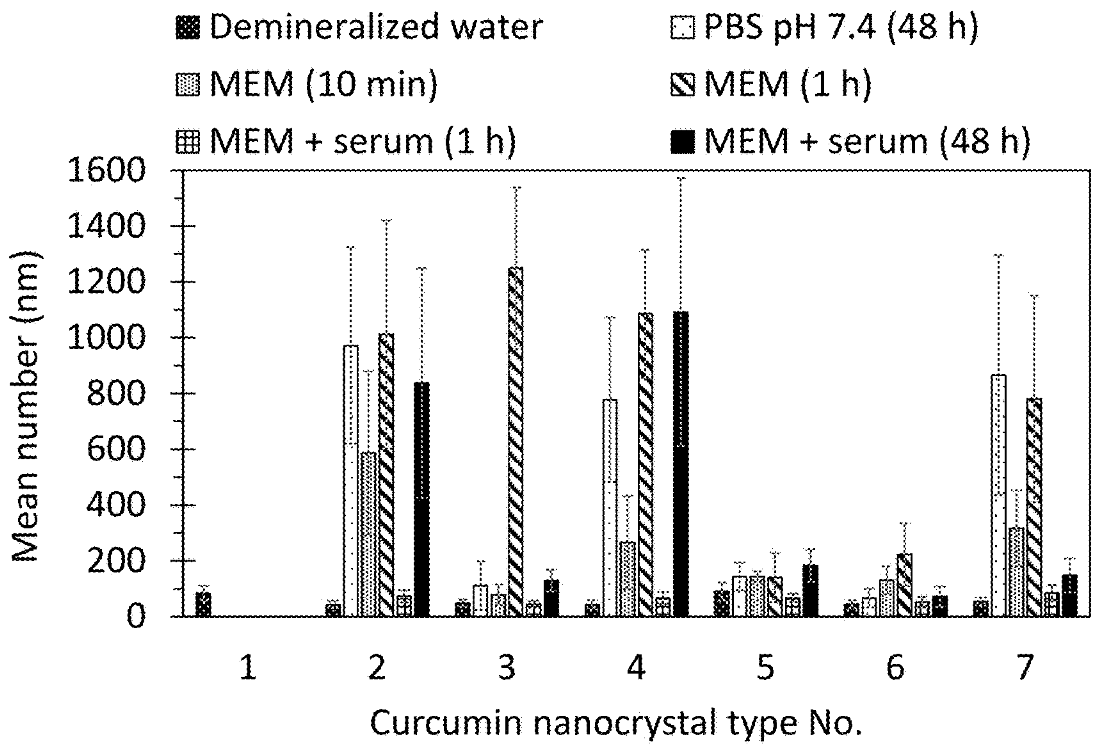
FIG. 18 Colloidal stability measurement results for differently stabilized curcumin nanocrystals (types 2-7) in different solvents. The chart shows number mean diameter and standard deviation in different solutions. Nanocrystal types 5 (DPPC:MPEG-DMPE) and 6 (DPPC:DPPG:MPEG-DMPE) preserve small particle size in all conditions which indicates great colloidal stability under all tested conditions. Other nanocrystal types exhibit increase in the particle size, which means loss of colloidal stability (aggregation/recrystallization).

It is well known that the colloidal stability of nanoparticles/nanocrystals strongly depends on the presence of salts and other dissolved molecules in the aqueous media. Since the main purpose of these nanocrystals was in vitro testing on cell lines, their stability in buffers and cell culture media (with or without protein content) was of high importance. The nanocrystal stability in physiological phosphate buffer saline (PBS pH 7.4, 10 mM), cell culture medium MEM, and MEM with serum (10% fetal bovine serum) were measured over time using DLS. Significant differences in the colloidal stability were observed when comparing different types of nanocrystal stabilizers. Nanocrystals stabilized with phospholipids exhibited the best behavior. The results are summarized in FIG. 18.

The worst overall stability was observed in the case of sample 1_Tween 80; these nanocrystals almost immediately aggregated in all types of media and buffers. Even in demineralized water, their properties were not sufficient to provide filtration product concentrated high enough to use this sample for cell line testing, which led to its exclusion from all subsequent experiments. The best colloidal stability was observed in case of phospholipidic stabilizations enriched with covalently attached polyethylene glycol; these nanocrystals proved to be stable under all experimental conditions over at least 48 h. A strong effect of the protein content (cell culture medium MEM+10% fetal bovine serum) on the colloidal stability improvement was observed in the case of all samples with previously compromised/low stability caused by the presence of salts. This could be explained by adsorption of positively charged protein form the medium to the negatively charged nanocrystals, which increased their stability.

Nanocrystals 3_SDS and 7_HPMC+DPPG were able to preserve colloidal stability in a medium with serum, but they aggregated in a medium without serum within less than one hour. A partial re-dispersibility from the sedimented pellet was observed in all cases, however, in most of them, the final nanocrystals never reached the initial particle size distribution when analyzed by DLS.

Example 2: Phagocytosis Assay

2.1 Methodology

The J774A.1 cells were harvested, counted, and diluted to $4\times10^5$ cells/mL in the DMEM+10% FBS+1% AA medium. Then, 100 μL of the cell suspension (equal to $4\times10^4$ cells) was pipetted to the desired number of the wells in a black plastic 96-well-plate, and the cells were left to adhere for 18 h in an incubator. The medium was then removed by aspiration and nanocrystal samples pre-diluted in DMEM+10% FBS+1% AA (50 μg/mL) were added to the well plate and incubated for various times (1 h, 2 h, 3 h, 4 h, 6 h). The phagocytosis assay was not carried out longer than for 6 hours due to possible macrophage apoptosis or the loss of the adherence when fully saturated by the nanocrystals, where this fact could lead to removal of the detached cells by the washing and subsequent incorrect data interpretation.

After the incubation, the wells were gently washed twice with PBS. Then, 50 μL of 1% SDS in demineralized water was added to each well and the cells were re-suspended by repeated pipetting. Then, 100 μL of ethanol for UV was added to each well to dissolve the curcumin nanocrystals. Finally, the fluorescence of the curcumin in the samples was measured by the well plate reader using excitation of 435 nm and emission of 545 nm. The amount of curcumin was calculated according to the calibration prepared in the same well plate using stock nanocrystals dissolved in 1% SDS: EtOH (1:2).

2.2 Results

Figure 19:
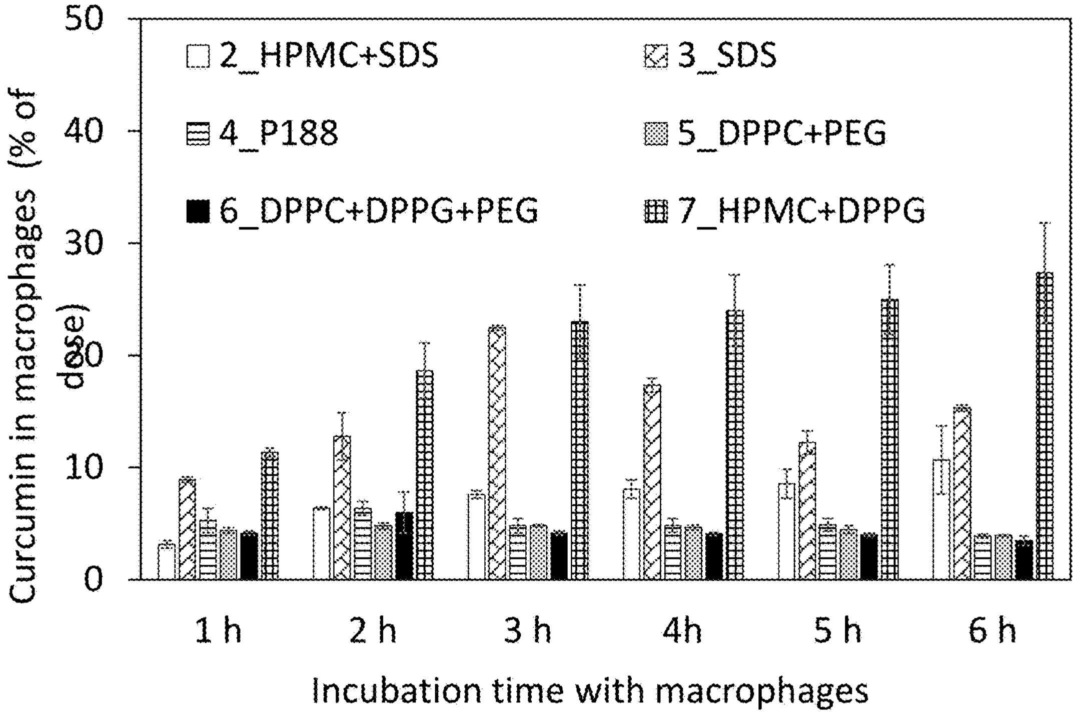
FIG. 19 Phagocytosis assay of curcumin nanocrystal types 2-7. Nanocrystal types 5 (DPPC:MPEG-DMPE) and 6 (DPPC:DPPG:MPEG-DMPE) are not significantly phagocytosed and only small amount of total curcumin in detected in the cells. Opposingly, there are several nanocrystal types, which suffer from high macrophage uptake (types 2, 3 and 7).

Non-specific immune responses to intravenously administered nanoparticles are connected to their recognition and removal by macrophages. The phenomenon of non-specific nanoparticle recognition by immune cells can be sufficiently mimicked in vitro in macrophage cell cultures when using culture media supplemented with fetal bovine serum. The results of phagocytosis experiments for all investigated curcumin nanocrystal formulations are shown in FIG. 19.

Macrophage phagocytosis and its kinetics was shown to be very dependent on the nanocrystal stabilization type. Two types of behavior were observed: strong association with macrophages (2_HPMC+SDS, 3_SDS, and 7_HPMC+DPPG), and weak or no non-specific macrophage uptake (4_P188, 5_DPPC:MPEG-DMPE, and 6_DPPC:DPPG:MPEG-DMPE).

The most significant phagocytosis was detected in the case of the sample 7_HPMC+DPPG where the maximum curcumin content was detected after 3 hours of the incubation and reached up to 25% of the dose which then remained constant. The amount of phagocytosed curcumin from the sample 3_SDS seems to reach the maximum in 3 hours (approximately 20% of the dose) and after then it decreases, which can be attributed to the curcumin decomposition or efflux from the cells.

On the other hand, in the case of the nanocrystals 4_P188, 5_DPPC:MPEG-DMPE, and 6_DPPC:DPPG:MPEG-DMPE the overall curcumin content never exceeded 5% of the dose, which indicate low macrophage phagocytosis when compared to other nanocrystal types. Low immune response to these formulations can be attributed to the stealth protein-repelling coating provided by the PEG-coupled phospholipids (samples 5 and 6), or by the amphiphilic surfactant poloxamer 188 (4_P188).

Example 3: Bioactivity of Curcumin Nanocrystals

3.1 Methodology—Cell Viability

As the nanocrystals fluorescence was shown to interfere with the resazurin assay commonly used for establishing cell viability, in this work, the viability was quantified using a bioreduction of WST-8 into formazan dye by live cells (measuring absorbance at 450 nm). No interferences in the conversion of this dye by the tested samples were detected.

For the purpose of the viability assay the harvested cells were counted using a hemacytometer in presence of Trypan blue (labels the dead cells). Then, appropriate amount of the cells was diluted in fresh medium and inoculated into 96-well plate for cell cultures (plastic, transparent) using a multichannel pipette ($1\times10^4$ cells per well for HT-29 and $8\times10^3$ cells per well of MRC-5, which cover higher area per cell). Some well were left empty for purpose of a nanocrystal background (well-plate coloring or non-washable sediment; to be subtracted in the final assay) and to provide zero absorbance values in the final assay.

The cells were left to adhere and acclimatize for 48 h in an incubator (5% $CO_2$, 37° C.). Then, the medium was removed by a gentle aspiration using a multichannel pipette and the nanocrystal samples pre-diluted in the medium were pipetted to the wells. Some wells were used to establish maximal viability in medium diluted with demineralized water to the same extent as occurs when the nanocrystal samples are diluted in medium, in order to mimic the change of the osmotic pressure and nutrient deprivation. These changes were found to be relevant only in case of HT-29 cells. The nanocrystals sediments which absorb the light in the similar range and were not completely washed away were used to measure a background; curcumin nanocrystals-treated wells without the cells were subtracted from the cell-provided results in the final assay. The pre-dilution was always done in a separate well-plate in excess volume to ensure sufficient amount to be transferred. The nanocrystals were studied in concentration range 50 μg/mL-1.6 μg/mL. The nanocrystal sample volume pipetted to the cell-containing wells was 90 μL/well.

The well-plate with the samples was kept in the incubator for 24 hours Then the cell medium was removed from the wells by aspiration, the whole well-plate was gently washed with PBS (200 μL/well) and the Cell Counting Kit-8 solution (containing WST-8) 10× diluted in PBS was added to all wells (100 μL/well). The well plate was placed in the incubator (MRC-5: 60 minutes; HT-29: 20 minutes) to allow for color development and then absorbance values were measured at 450 nm (reference at 650 nm) using Tecan Infinite M200 well-plate reader.

3.2 Results—Cytotoxicity and Bioactivity of Curcumin Nanocrystals

Figure 20:
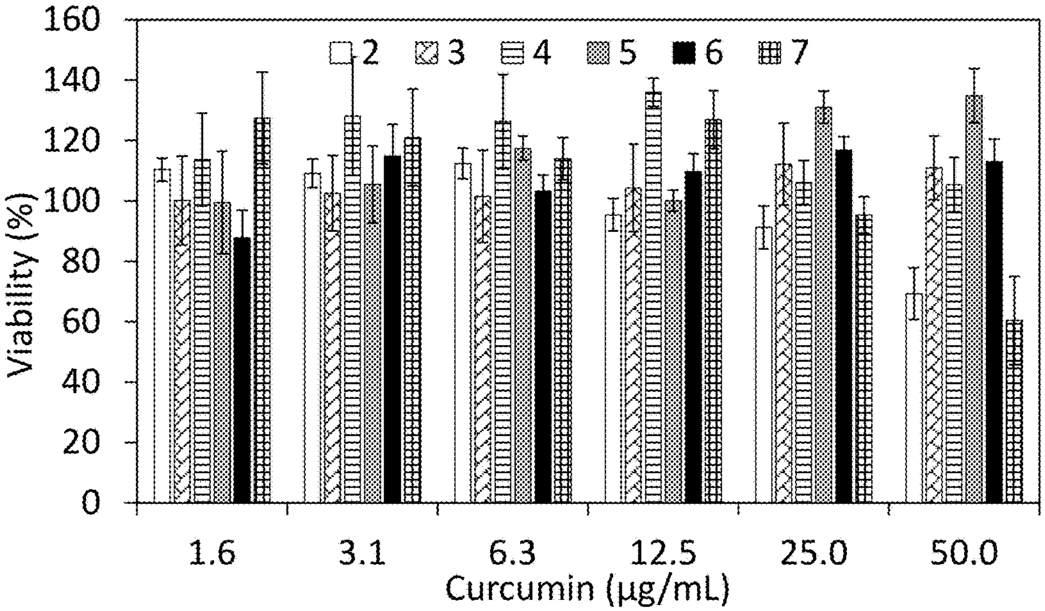
FIG. 20 Cytotoxicity of curcumin nanocrystal types 2-7 against MRC-5 non-cancerous cells. Nanocrystal types 5 (DPPC:MPEG-DMPE) and 6 (DPPC:DPPG:MPEG-DMPE) do not exhibit any cytotoxicity to healthy cells in the tested concentration range. On the other hand, nanocrystal types 2 and 7 exhibit some cytotoxicity in high concentrations.

The viability assay in non-cancerous cell line reflects the toxicity of a formulation against healthy tissues. The qualitative microscopic images and the quantitative cytotoxicity data obtained from cytotoxicity assay are show in FIG. 20. Nanocrystal types 3, 4, 5, and 6 did not exhibit cytotoxicity in the studied range of concentrations.

Nanocrystals 2 and 7 exhibited a dose-dependent cytotoxicity; at concentration of 50 μg/mL these samples exhibited weak and moderate cytotoxicity, respectively (according to ISO 10993-5, values of cell viability above 80% are considered as non-cytotoxicity; within 80%-60% weak; 60%-40% moderate and below 40% strong cytotoxicity respectively. The half maximal inhibitory concentration ($IC_{50}$) values were calculated from the obtained data as follows: $IC_{50}$ (2_HPMC+SDS)=71.7±6.7 μg/mL, $IC_{50}$ (7_HPMC+DPPG)=59.3±8.5 μg/mL.

From the results of the cytotoxicity, it can be concluded that samples 3_SDS, 4_P188, 5__DPPC:MPEG-DMPE and 6_DPPC:DPPG:MPEG-DMPE are non-toxic to healthy cells, and therefore represent perspective candidates for pharmaceutically viable formulations provided that they exhibit bioactivity toward the target (disease) cells.

Further bioactivity testing of curcumin nanocrystals focused on its anti-proliferative and pro-apoptotic effect on colorectal carcinoma cell line HT-29. In this series of experiments the cells were treated with curcumin nanocrystal-based formulations in concentration range 50-1.6 μg/mL for 24 hours. It should be noted that this is well above the thermodynamic solubility of curcumin in water. Although such concentration could be potentially reached by using DMSO, this approach is prone to uncontrolled precipitation of the dissolved substance upon dilution in the cell culture medium. The use of colloidally stable pre-formulated nanocrystals enables well controlled bioactivity experiment to be carried out.

Figure 21:
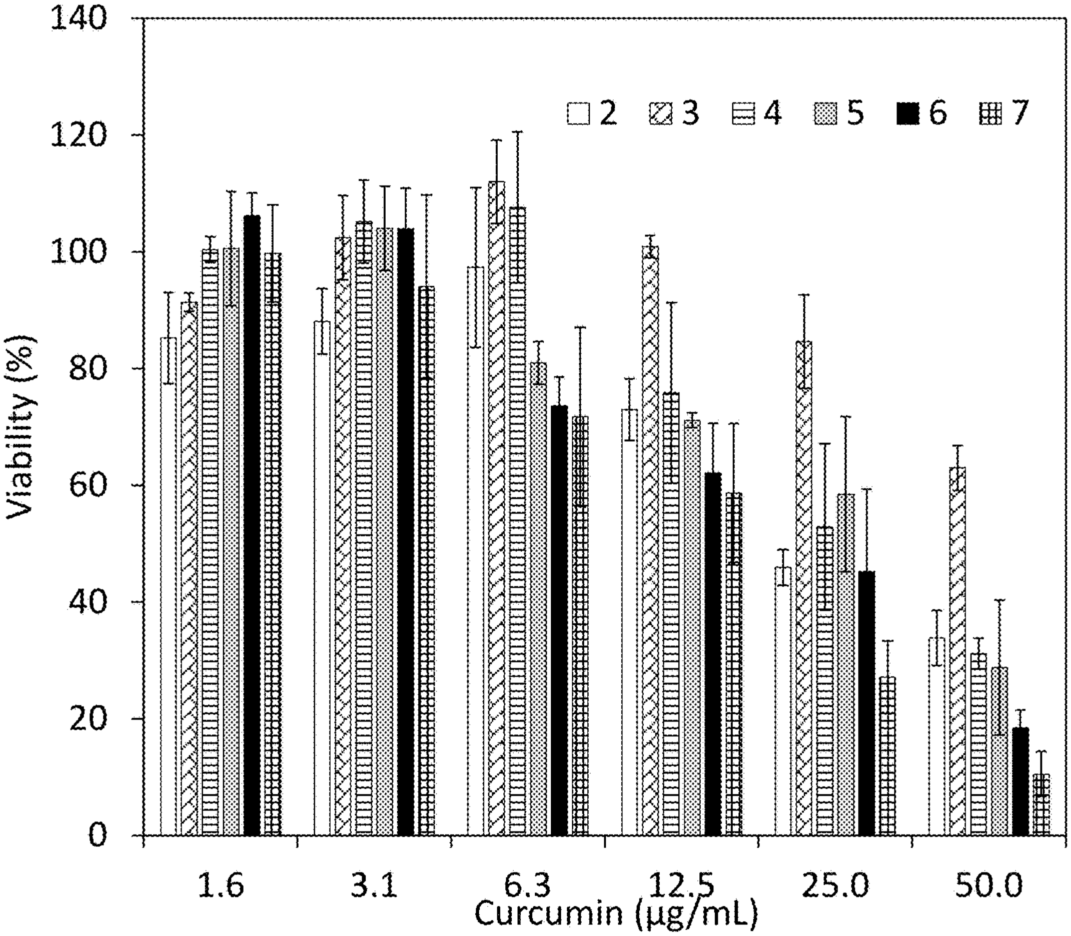
FIG. 21 Cytotoxicity of curcumin nanocrystal types 2-7 against HT-29 colorectal carcinoma cells. Curcumin nanocrystals exhibit high efficiency comparable to commonly used chemotherapy agents. Such efficiency has not been observed before when studying only curcumin from DMSO solutions.

The cell viability was measured by WST-8 viability assay. The obtained data are summarized in FIG. 21.

A significant dose-dependent effect on cell viability decrease was observed for all tested nanocrystal samples. The values ranged between 20-70 μg/mL (70-190 μM). The exact $IC_{50}$ values for curcumin nanocrystal types were as follows: 32.6±5.3 (2_HPMC+SDS), 68.2±6.0 μg/mL (3_SDS), 34.3±5.6 μg/mL (4_P188), 32.9±5.3 μg/mL (5_DPPC:MPEG-DMPE), 27.1±4.1 μg/mL (6_DPPC:DPPG:MPEG-DPME), and 22.1±5.7 μg/mL (7_HPMC+DPPG).

The lowest $IC_{50}$ (22.1±5.7 μg/mL) was observed for 7_HPMC+DPPG nanocrystals. This information when taken out of the context could falsely indicate that this stabilization provides the most efficient nanocrystal-based formulation for cancer treatment. However, this formulation exhibited the strongest non-specific macrophage uptake and the highest cytotoxicity against MRC-5, which are both undesirable qualities for a drug delivery system.

Figure 22:
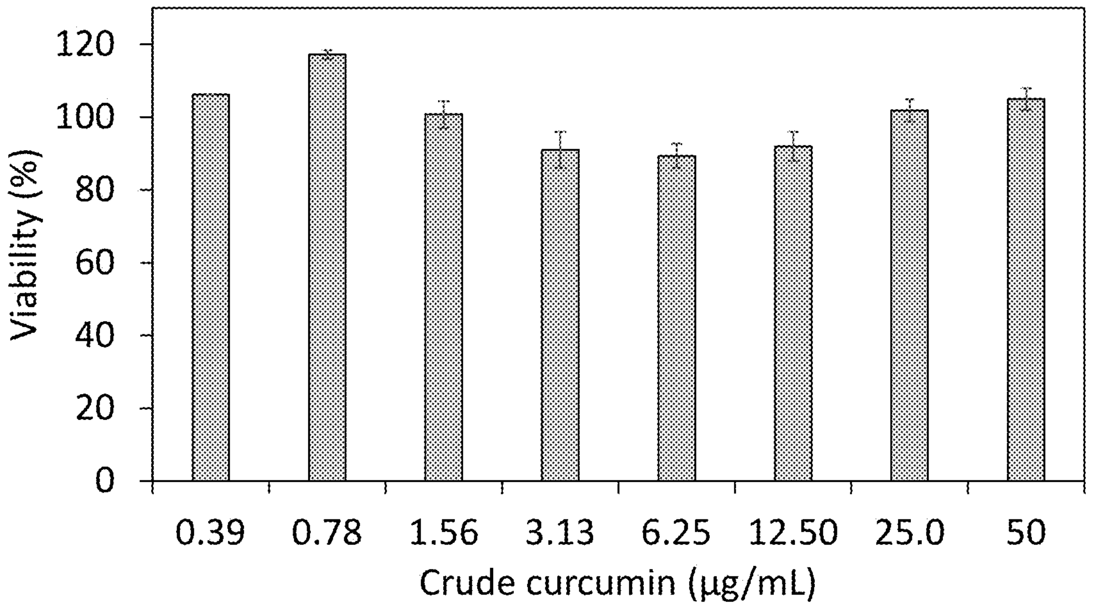
FIG. 22 Cytotoxicity of crude curcumin added to the cell culture medium as a dispersion of macroscopic crystals as purchased. No significant effect on the cellular viability is detected over 48 h of incubation.

The second lowest $IC_{50}$ was detected for the sample 6_DPPC:DPPG:MPEG-DMPE with a value of 27.1±4.1 μg/mL (73 μM). This nanocrystal type also proved to be non-toxic to healthy cells and crucially, non-phagocytosed. To compare, crude curcumin (macroscopic crystals that are input material for the wet-milling) dispersed in medium did not show any effect in the tested concentration range not even in 48 hours (FIG. 22). To further put these results in context of cancer treatment feasibility, it is important to emphasize that some of the clinically used drugs exhibit similar or even lower cisplatin was documented to have $IC_{50}$=181 μM, 5-fluorouracil 39 μM, and gefitinib >100 μM, Silybinin, an active compound from *Silybum marianum* exhibited $IC_{50}$=180 μM, curcumin dissolved in DMSO has been tested on the human cancer cell lines TK-10, MCF-7 and UACC62, and after 48 hours the $IC_{50}$ values were 12.2 mM, 3.6 mM, 4.3 mM, respectively, It must be noted that $IC_{50}$ values are always lower for 48 h incubation than for 24 h incubation. These findings clearly show the tremendous improvement of the anticancer potential of curcumin when formulated into nanocrystals.

Example 4: Overall Evaluation of Curcumin Nanocrystals Performance

Using the information provided by the colloidal stability studies, non-specific macrophage phagocytosis, cytotoxicity, and anticancer assays, samples 5_DPPC:MPEG2000-DMPE and 6_DPPC:DPPG:MPEG2000-DMPE were the only ones to successfully pass all the assays necessary to be safely considered for further applications (see Table 7). These samples proved to have uncompromised colloidal stability in all studied buffers and cell culture media. Moreover, these nanocrystals did not show any toxicity to the healthy cells and at the same time exhibited exceptionally high bioactivity against colorectal carcinoma HT-29 cell line. Space bars indicate situations where the sample did not exhibit properties allowing its further testing.

TABLE 7

Curcumin nanocrystals' performance in tests for stability and interaction with cells.

| | 1 | 2 | 3 | 4 | 5 | 6 | 7 |
|---|---|---|---|---|---|---|---|
| Filtration yield, stability in buffers and media | x | x | ✓ | x | ✓ | ✓ | ✓ |
| Macrophage uptake | — | x | x | ✓ | ✓ | ✓ | x |
| Cytotoxicity to healthy cells | — | x | ✓ | ✓ | ✓ | ✓ | x |
| Cytotoxicity to cancer cells | — | ✓ | ✓ | ✓ | ✓ | ✓ | ✓ |

Example 5: Precipitation From DMSO Solutions Analyzed by Microscopy

5.2 Methodology

For the purpose of the crystallization form DMSO solution study, the J774A.1 cells in the DMEM+10% FBS+1% AA medium were inoculated in a 96 well-plate with a glass-bottom (Cellvis, P96-1.5H-N) with a density of $2\times10^4$ cells/well and left to adhere overnight. Then, the medium was removed by aspiration, and nanocrystal samples prediluted in the fresh medium were added (from 500 μg/mL decreasing in half concentration trend; 90 μL/well). In some cases (abiraterone acetate, telmisartan), it was not possible to reach 500 μg/mL API concentration together with total DMSO content of maximum 1% (1% DMSO is top limit standard in biochemical testing considering the DMSO toxicity and effect on the cell viability and performance) and therefore these substances were tested at 100 μg/mL concentration. Here the great potential of nanocrystals is clearly presented, since the nanocrystal samples were possible to be prepared and tested at 500 μg/mL even in cases where the DMSO solvents would not be accepted for in vitro testing.

5.3 Results

The results of microscopic analysis of nanocrystalline samples versus 1% DMSO solution are summarized in FIG. 23-FIG. 28. If possible, all samples were tested at concentration 500 μg/mL (from nanocrystals or from DMSO stock solutions) and incubated in the well-plate for 18 h. In some cases (abiraterone, telmisartan), it was not possible to reach concentration 500 μg/mL and at most 1% DMSO content in the tested sample due to low solubility of these substances in DMSO (these APIs were tested at 100 μg/mL in 1% DMSO)—however, such concentration can be easily reached using nanocrystals.

The tested APIs were those listed in Table 1. The nanosuspensions were stabilized by the combination DPPC:DPPG:MPEG2000-DMPE in molar ratio 85:10:5. The formation of macroscopic crystals from the DMSO solutions is markable, while the nanocrystalline suspensions do not cause formation of new crystals. The morphology and the amount of the newly developed solid phase differs according to the solvent.

Figure 23:
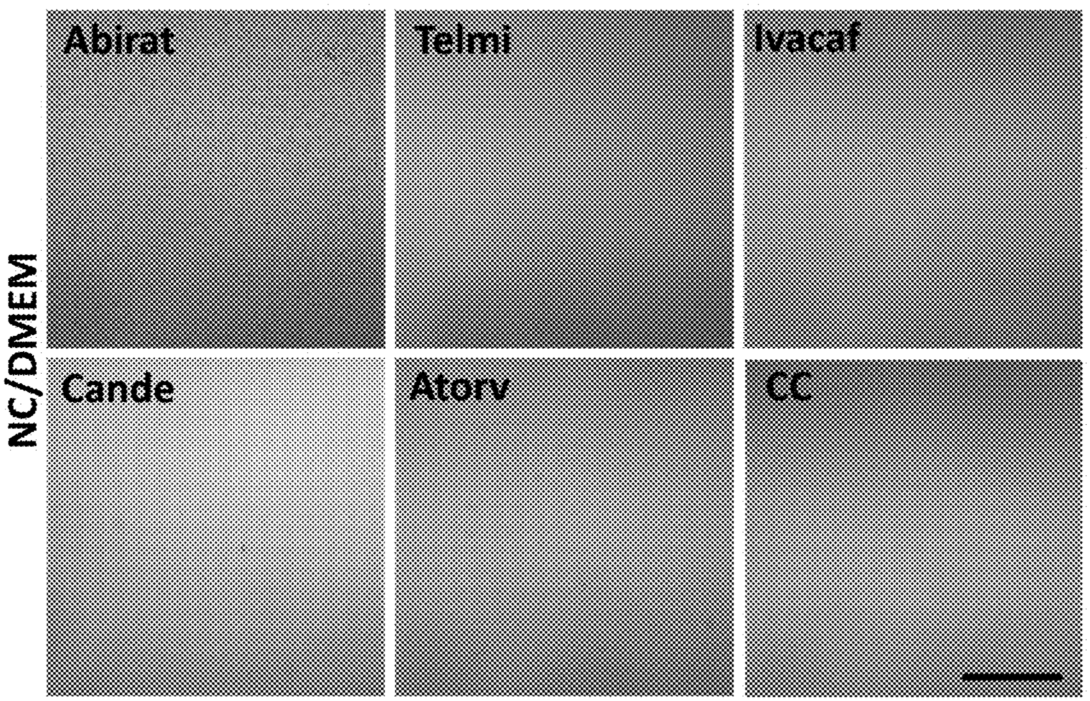
FIG. 23 Microscopic images of API nanocrystals in DMEM medium supplemented with 10% fetal bovine serum. API concentration is 500 μg/mL. No recrystallization occurs. Scale bar is 50 μm.
Figure 29:
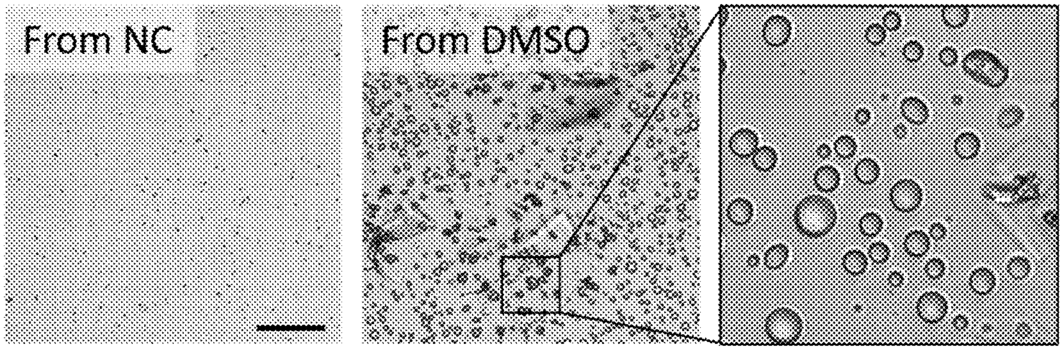
FIG. 29 Detail of abiraterone acetate oiling out. When added from DMSO solution, formation of both new crystals and solid amorphous phase occurs. When added from nanocrystals, no crystal formation occurs and oiling out is minimized Scale bar is 5 μm.

FIG. 23 shows the nanocrystals suspension (500 μg/mL) in DMEM medium supplemented with 10% fetal bovine serum, where no recrystallization is detected and nanocrystals preserve colloidal stability over tested time. The only visually detectable change was observed in case of abiraterone acetate, where it was found to form amorphous "droplets" of the drug on the microscopic glass. The similar behavior, but to a higher extent was observed in case of its DMSO solution. This phenomenon is called "oiling out", where when exceeding the thermodynamic solubility, some lipophilic substances form solid amorphous phase rather than crystals (FIG. 29).

Figure 24:
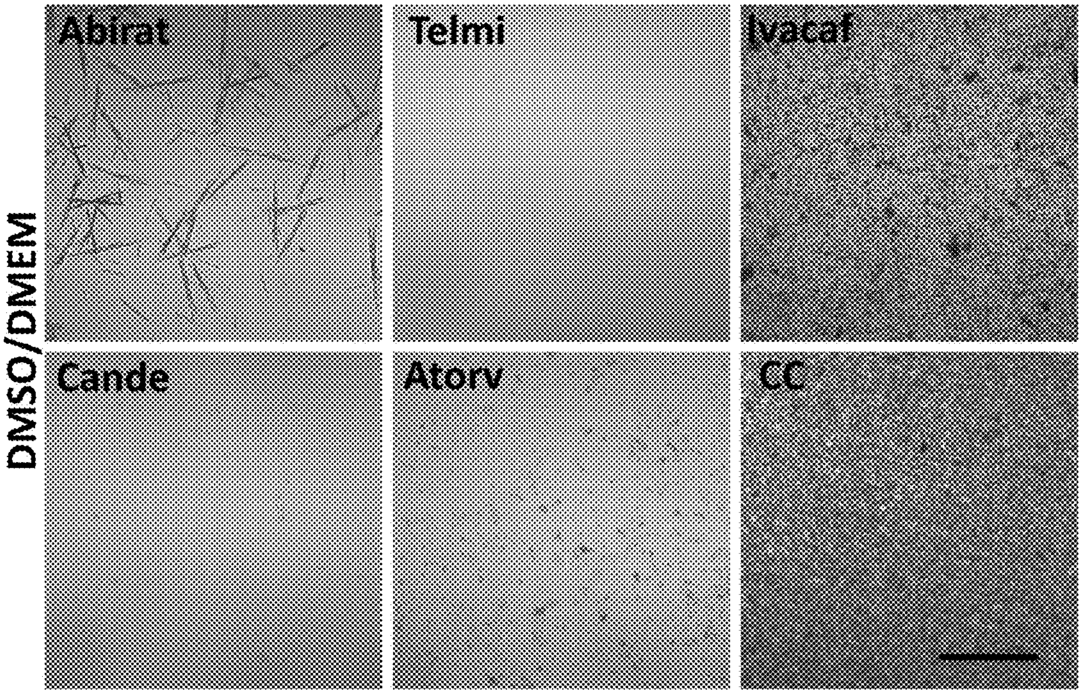
FIG. 24 Microscopic images of APIs added from DMSO into DMEM medium supplemented with 10% fetal bovine serum. API concentration is 100 μg/mL for abiraterone acetate and telmisartan and 500 μg/mL for all other. In the most cases, recrystallization is detected. Scale bar is 50 μm.
Figure 25:
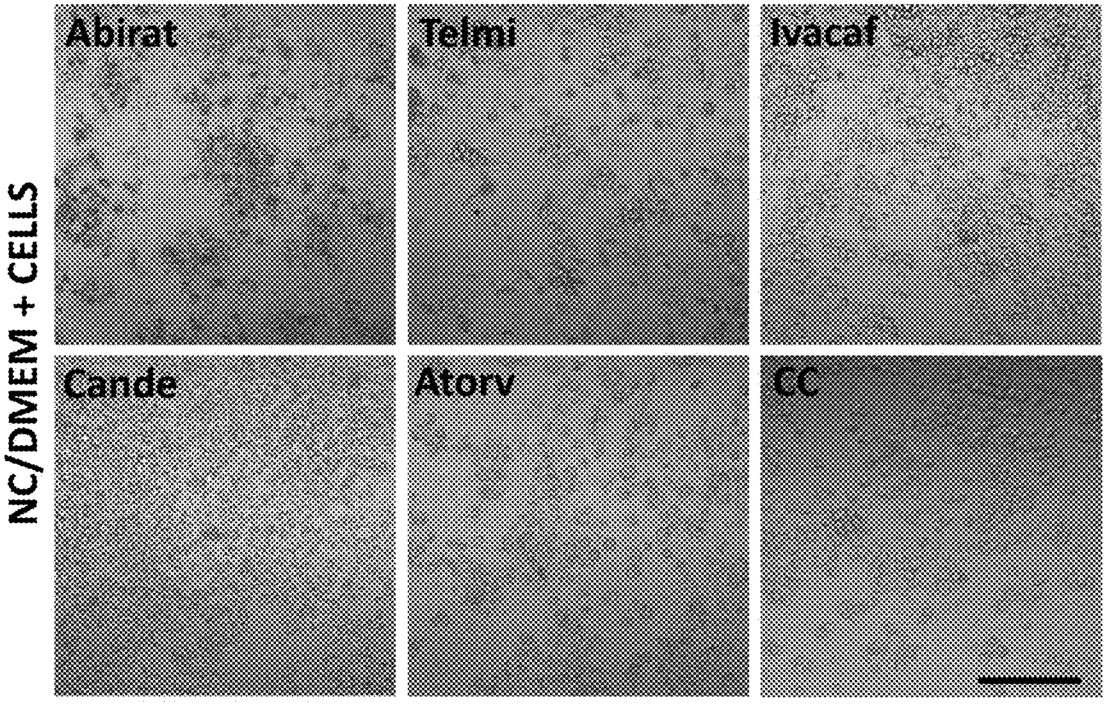
FIG. 25 Microscopic images of API nanocrystals tested with macrophages J774A.1 in DMEM medium supplemented with 10% fetal bovine serum. API concentration is 500 μg/mL. No recrystallization occurs. Scale bar is 50 μm.

On the other hand, FIG. 24 shows addition of the substances from the DMSO stock solutions, where precipitation/recrystallization is markable (only telmisartan and candesartan cilexetil did not form macroscopic crystals in DMEM medium without cells).

Figure 26:
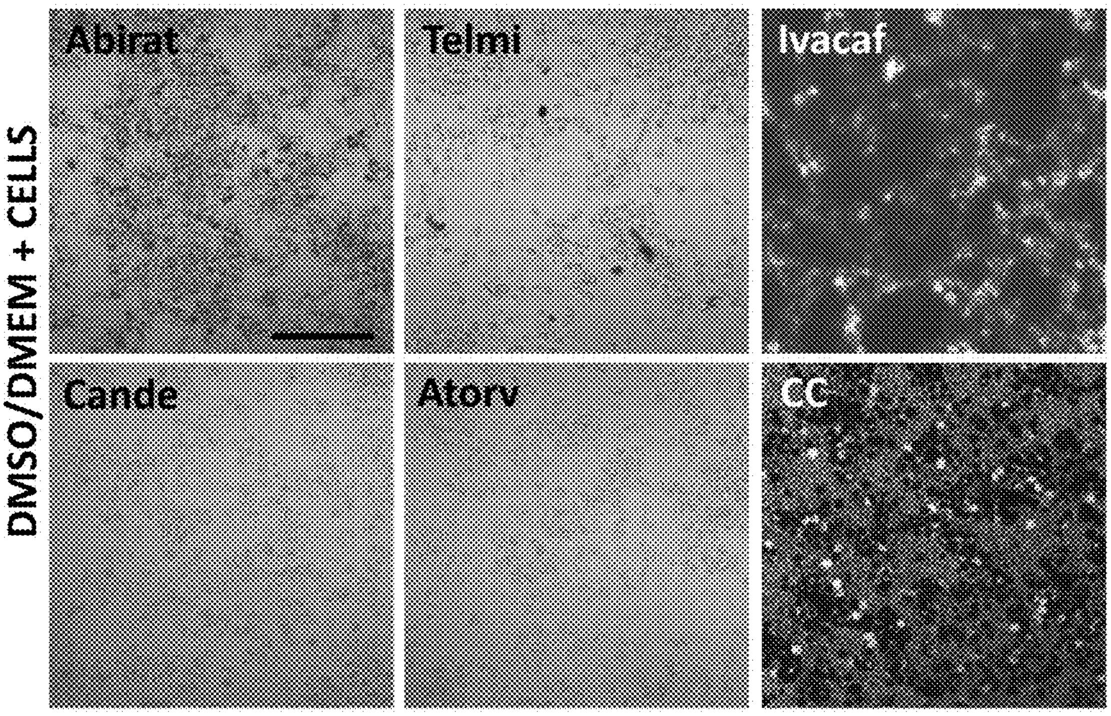
FIG. 26 Microscopic images of APIs added from DMSO, tested with macrophages J774A.1 in DMEM medium supplemented with 10% fetal bovine serum. API concentration is 100 μg/mL for abiraterone acetate and telmisartan and 500 μg/mL for all other. The most significant recrystallization/precipitation is detected in case of ivacaftor and curcumin. Scale bar is 50 μm.
Figure 27:
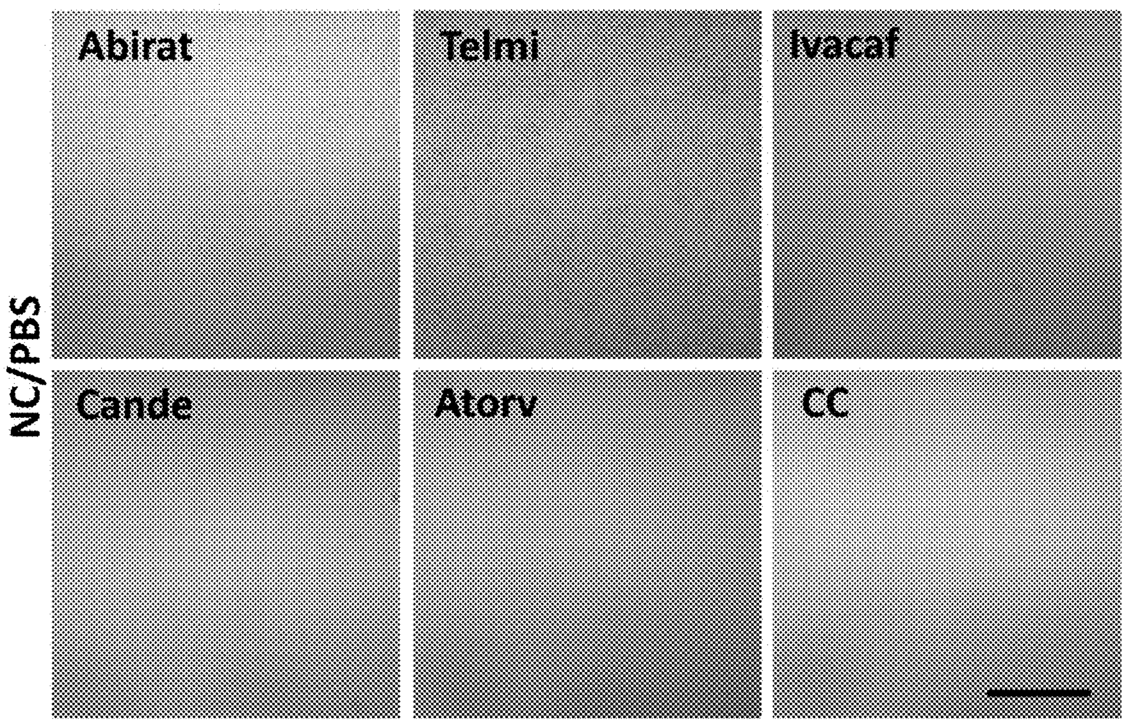
FIG. 27 Microscopic images of API nanocrystals PBS pH 7.4. API concentration is 500 μg/mL. No recrystallization occurs. Abiraterone acetate oiling out is detected, partial destabilization of telmisartan nanocrystals is detected. Scale bar is 50 μm.
Figure 28:
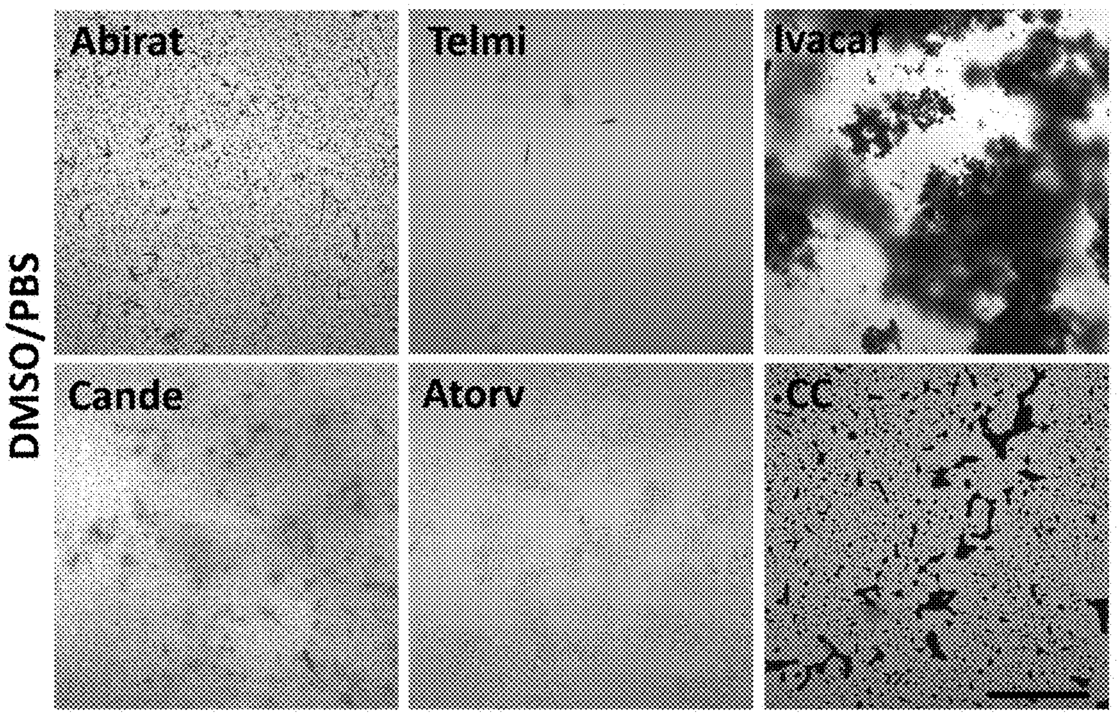
FIG. 28 Microscopic images of APIs added from DMSO into PBS pH 7.4. API concentration is 100 μg/mL for abiraterone acetate and telmisartan and 500 μg/mL for all other. Recrystallization/precipitation or oiling out is detected in most of the cases. Scale bar is 50 μm.
Figure 30:
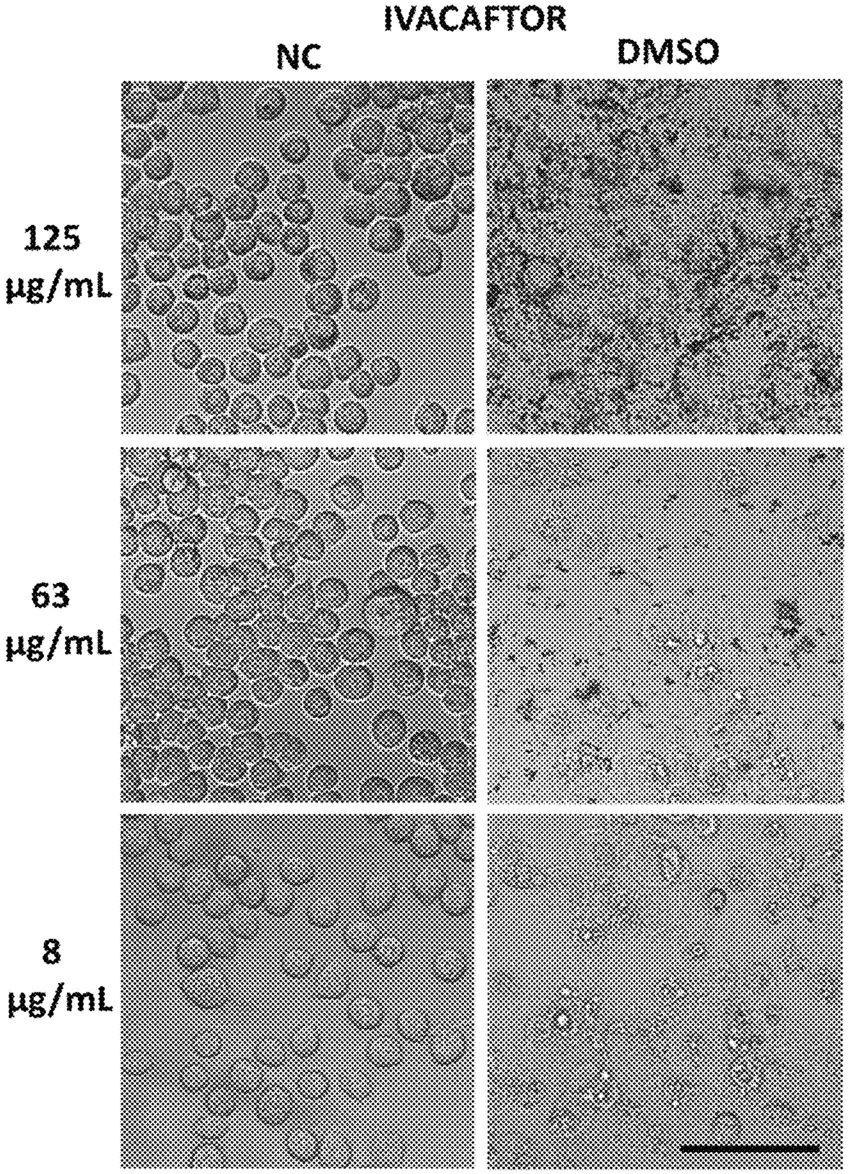
FIG. 30 Microscopic images of cells incubated with ivacaftor added in form of nanocrystals (left) and DMSO solution (right) showing lower concentrations (8-125 μg/mL). In whole concentration range the DMSO solutions causes cell death (membrane blobbing), while the same concentrations added in form of nanocrystals do not harm the cells. Scale bar is 50 μm.

When tested with cells all nanocrystal samples performed well (FIG. 25), but precipitation/recrystallization from DMSO occurred and was well detectable in case of ivacaftor and curcumin (FIG. 26). In most of the cases the cells underwent cell death, which was caused either by the API itself (for example abiraterone acetate is highly potent anticancer drug with high toxicity), or by mechanical disruption of cellular membranes by newly created crystals. This was the most markable in case of ivacaftor. FIG. 30 shows microscopic images of cells incubated with ivacaftor added in form of nanocrystals (left) and DMSO solution (right) showing lower concentrations (8-125 μg/mL). In the whole studied concentration range the DMSO solutions causes cell death (membrane blobbing), while the same concentrations added in form of nanocrystals did not harm the cells. This clearly shows that the recrystallization form DMSO solutions is a serious problem in in vitro testing and may lead to incorrect data interpretation.

Testing in PBS resulted in similar results, in favor of nanocrystals (FIG. 27, FIG. 28)—in all cases of DMSO solution recrystallization/precipitation was detected. On the other hand, most of the nanocrystals in PBS exhibited great colloidal stability; telmisartan nanocrystals exhibited partial sedimentation, but no recrystallization occurred.

To conclude, all nanocrystalline samples exhibited superior performance than DMSO solutions and would form suitable candidates of in vitro testing of poorly soluble drugs.

Comparative Example

Figure 31:
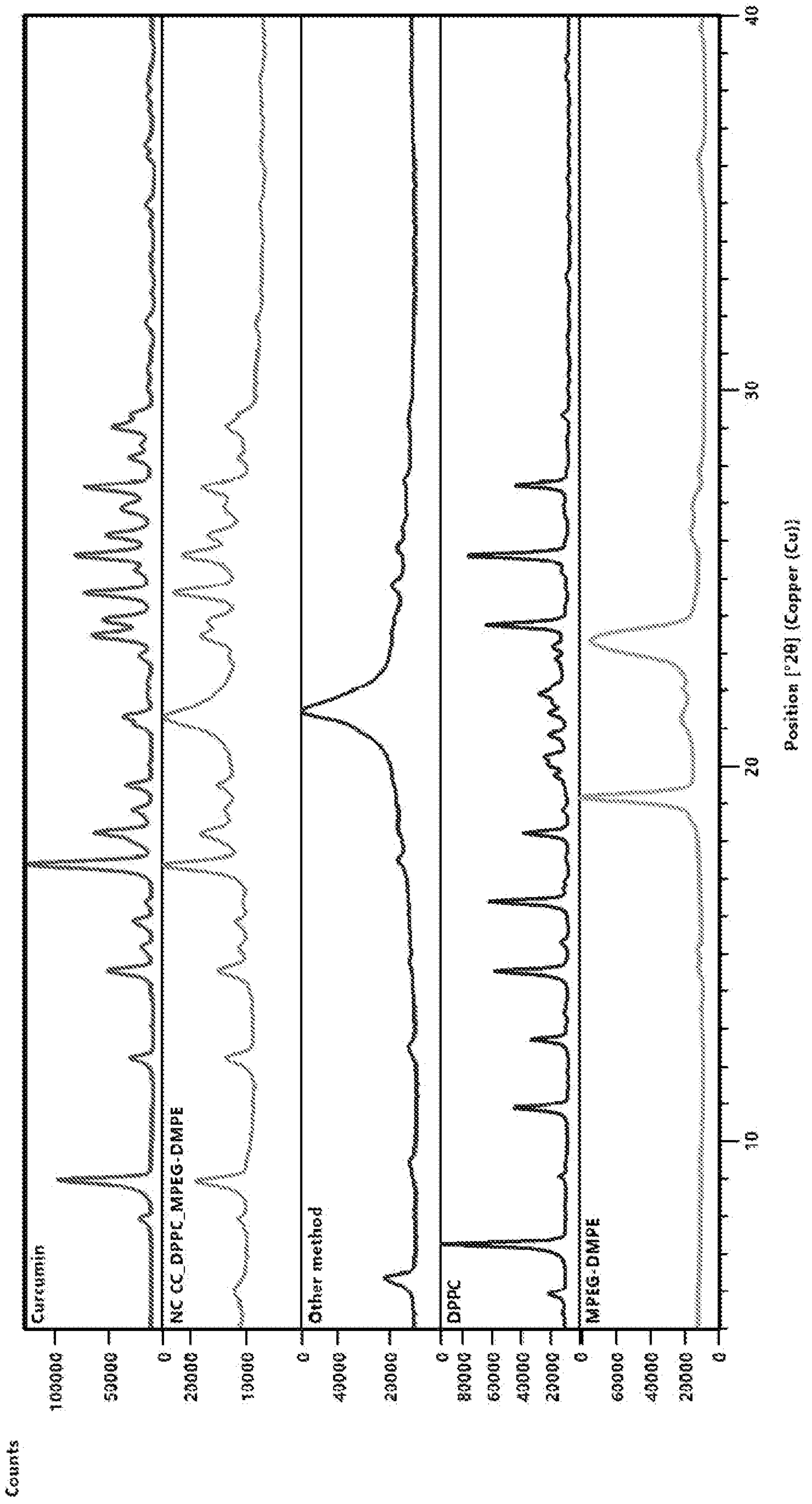
FIG. 31 XRD characterization of samples according to Comparative experiment.

In order to demonstrate that high concentrations of phospholipids lead to formation of nanoemulsions rather than to the formation of nanocrystalline suspension, the following comparative experiment was performed:

300 mg of dipalmitoylphosphatidylcholine (DPPC), 9 mg of pegylated phospholipid MPEG-DMPE and 30 mg of curcumin (the weight ratio of curcumin to the combination of stabilizing agents was 30:309, thus a high excess of phospholipids was used) were milled in 60 mL of demineralized water (the concentration of curcumin (API) in aqueous suspension was thus 0.5 mg/mL), using wet milling procedure as described in the present invention. The sample was then freeze-dried and characterized by XRD (in the text below referred to as "other method", third XRD spectrum from the top in FIG. 31).

Furthermore, another sample was prepared by the method according to the present invention, using 60 mg of curcumin, 33.5 mg of dipalmitoylphosphatidylcholine (DPPC), and 6.5 mg of pegylated phospholipid MPEG-DMPE (the weight ratio of curcumin to the combination of stabilizing agents was 3:2 as in the present invention). Wet milling was performed, and the resulting nanocrystalline sample had XRD spectrum referred to as "NC_CC_DPPC_MPEG-DMPE", depicted as second spectrum from the top in FIG. 1).

FIG. 1 further contains record of pure crystalline curcumin (top spectrum), and individual phospholipids used for the stabilization (DPPC; MPEG-DMPE).

It was observed that the differences in the crystalline phase content between the samples were very significant. The sample prepared by the method according to the present invention exhibits strong curcumin crystals phase record, while the sample prepared using low API concentration and high phospholipid content provides for very low crystal phase content, wherein the curcumin crystal phase is negligible.

The invention claimed is:

1. A method for preparing an aqueous nanocrystalline suspension of API, comprising the following steps:

(a) preparing an aqueous suspension comprising a crystalline API, selected from the group comprising API having intrinsic solubility in water at most 50 mg/L, and having log P at least 4;

and a combination of at least two stabilizing agents, selected from the group of phospholipids containing lipophilic carbohydrate chains comprising from 6 to 20 carbon atoms;

wherein at least one of the stabilizing agents is selected from the group of PEG-coupled phospholipids of general formula (I), (I)

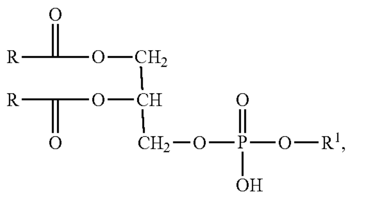

wherein R is independently selected from (C6 to C20) alkyl and (C6 to C20)alkenyl;

R 1 is

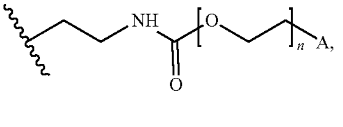

n is an integer in the range of from 8 to 125;

A is selected from the group comprising —OH; —$OCH_3$; —$NH_2$; —NH—(C═O)—$CH_2$—$CH_2$—COOH; —NH—(C═O)—$CH_2$—$CH_2$—SH; —$CH_2COOH$; —$N_3$, —O—$CH_2COOH$; —$CH_2CH$(═O);

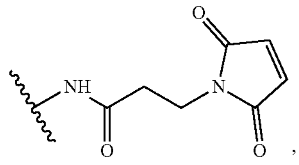,

-continued

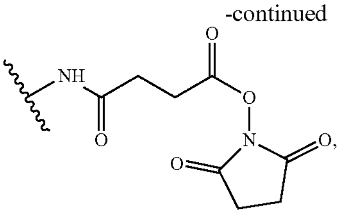

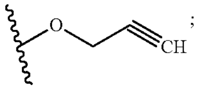;

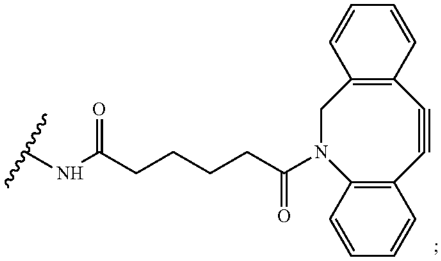;

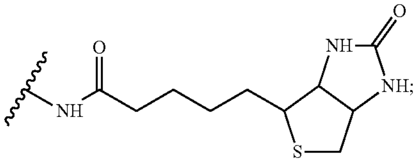

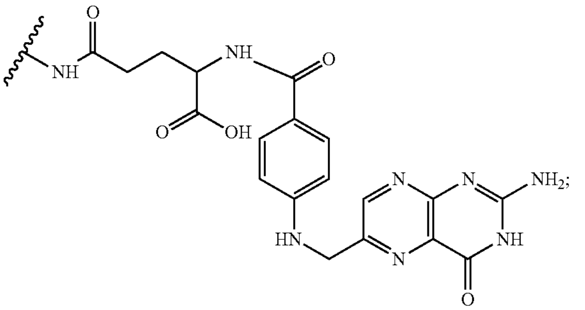

wherein the weight ratio of API to the combination of stabilizing agents is in the range of from to 20:1 to 10:1; and wherein the concentration of crystalline API in the aqueous suspension in step (a) is in the range of from 10 mg/mL to 100 mg/mL;

(b) placing milling balls into the aqueous suspension from step (a), and (c) milling the aqueous suspension of step (b) to obtain nanocrystalline API suspension, wherein the size of the API nanocrystals is at most 300 nm, determined using dynamic light scattering in demineralized water at 20° C.

2. The method according to claim 1, wherein step (c) is followed by a step (d), wherein the resulting suspension from step (c) is sterile-filtered with a filter of the average pore size of 200 nm, resulting in the size of the API nanocrystals of at most 200 nm, determined using dynamic light scattering in demineralized water at 20° C.

3. The method according to claim 1, wherein the molar ratio of the PEG-coupled phospholipids of general formula (I) to the non-PEG-coupled phospholipids is in the range of from 1:24 to 1:9.

4. The method according to claim 1, wherein API is selected from the group comprising curcumin, abiraterone acetate, ivacaftor, atorvastatin, candesartan cilexetil, and telmisartan.

5. The method according to claim 1, wherein the PEG-coupled phospholipid has general formula (I), wherein R is independently selected from linear (C6 to C20)alkyl and linear (C6 to C20)alkenyl.

6. The method according to claim 1, wherein the non-PEG-coupled phospholipidic stabilizing agent has the general formula (II)

(II)

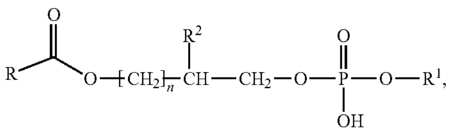

wherein n is an integer from 1 to 3;

$R^1$ is selected from the group comprising H; $-(CH_2)_m-NH_2$; $-(CH_2)_m-CH(OH)-CH_2(OH)$; $-(CH_2)-CH(COOH)-NH_2$;

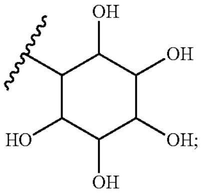

wherein m is an integer from 1 to 3;

$R^2$ is selected from —OH; —O—C(=O)—R;

R is independently selected from (C6 to C20)alkyl and (C6 to C20)alkenyl.

7. The method according to claim 1, wherein the combination of stabilizing agents in step (a) comprises from 2 to 20 mol. %, based on the total phospholipid contents, of the PEG-coupled phospholipid of general formula (I), from 0 to 20 mol. %, based on the total phospholipid contents, of an anionic phospholipid, selected from the group consisting of phospholipids with hydrophilic headgroup selected from phosphatidic acid, lysophosphatidic acid, phosphatidylglycerol, lysophosphatidylglycerol, phosphoinositide, lysophosphoinositide, phosphatidylserine, lysophosphatidylserine; and with lipophilic carbohydrate chains containing from 6 to 20 carbon atoms; and from 60 to 98 mol. %, based on the total phospholipid contents, of a phospholipid, selected from the group consisting of phospholipids with hydrophilic headgroup selected from phosphatidylethanolamine, lysophosphatidylethanolamine, phosphatidylcholine, lysophosphatidylcholine, and with lipophilic carbohydrate chains containing from 6 to 20 carbon atoms.

8. An aqueous pharmaceutical nanocrystalline suspension of API, consisting of nanocrystalline API selected from the group consisting of API, which have their intrinsic solubility in water of at most 50 mg/L, and having log P of at least 4;

and a combination of at least two stabilizing agents, selected from the group of phospholipids containing lipophilic carbohydrate chains consisting of from 6 to 20 carbon atoms;

wherein at least one of the stabilizing agents is selected from the group of PEG-coupled phospholipids of general formula (I) as defined in claim 1;

wherein the weight ratio of API to the combination of stabilizing agents is in the range of from 20:1 to 10:1, wherein the molar ratio of the PEG-coupled phospholipids of general formula (I) to the non-PEG-coupled phospholipids is in the range of from 1:49 to 1:4, and wherein the nanoparticle size is at most 300 nm, measured by DLS in demineralized water at 20 °C.

9. The aqueous pharmaceutical nanocrystalline suspension of API according to claim 8, wherein the concentration of nanocrystalline API is in the range of from 10 mg/mL to 100 mg/mL.

10. The aqueous pharmaceutical nanocrystalline suspension of API according to claim 8, wherein the combination of phospholipidic stabilizing agents comprises from 4 to 10 mol. %, based on the total phospholipid contents, of PEG-coupled phospholipid of general formula (I) according to claim 1, wherein R is —(CH)14—CH3, and n is in the range of from 40 to 80; from 80 to 94 mol. %, based on the total phospholipid contents, of dipalmitoylphosphatidylcholine, and from 2 to 10 mol. %, based on the total phospholipid contents, of dipalmitoylphosphatidylglycerol.

11. The aqueous pharmaceutical nanocrystalline suspension of API according to claim 8, wherein the combination of phospholipidic stabilizing agents comprises dipalmitoylphosphatidylcholine, dipalmitoylphosphatidylglycerol and PEG-coupled phospholipid of general formula (I) according to claim 1, wherein the molar ratio of dipalmitoylphosphatidylcholine: dipalmitoylphosphatidylglycerol: PEG-coupled phospholipid is 85:10:5;

and wherein API is selected from the group consisting of curcumin, abiraterone acetate, ivacaftor, atorvastatin, candesartan cilexetil, and telmisartan.

12. A pharmaceutical composition, containing the aqueous pharmaceutical nanocrystalline suspension of API according to claim 8, further comprising at least one pharmaceutically acceptable excipient.

13. A method for in vitro development, screening and bioactivity testing of new natural or synthetic drugs or new drug forms of API, comprising the step of providing the aqueous pharmaceutical nanocrystalline suspension of API according to claim 8.

14. A method for stabilizing aqueous nanocrystalline suspensions of low water soluble nanocrystalline compounds, comprising the step of providing a nanocrystalline compound having intrinsic solubility in water of at most 50 mg/L and having log P of at least 4, and the step of providing stabilizing agents selected from the group of phospholipids containing lipophilic carbohydrate chains comprising from 6 to 20 carbon atoms;

wherein at least one of the stabilizing agents is selected from the group of PEG-coupled phospholipids of general formula (I), as defined in claim 1;

wherein the content of the PEG-coupled phospholipids of general formula (I) is in the range of from 2 to 20 mol. %, related to the overall content of phospholipidic stabilizing agents in the combination;

and wherein the weight ratio of said nanocrystalline compound to the combination of stabilizing agents is in the range of from 20:1 to 10:1.

15. The method for stabilizing aqueous nanocrystalline suspensions of low water soluble nanocrystalline compounds according to claim 14, wherein the lipophilic carbohydrate chains are independently selected from $-(CH_2)_{14}-CH_3$; $-(CH_2)_{16}-CH_3$; $-(CH_2)_3-(CH{=}CH-CH_2)_4-(CH_2)_3-CH_3$; and $-(CH_2)_7-CH{=}CH-(CH_2)_7-CH_3$.

16. The method according to claim 5, wherein R is independently selected from the group consisting of $-(CH_2)_z-CH_3$, wherein z is an integer in the range of from 10 to 17; $-(CH_2)_p-(CH{=}CH-CH_2)_q-(CH_2)_r-CH_3$, wherein p and r are independently an integer from 1 to 8; and q is an integer from 1 to 5 .

* * * * *